(12) United States Patent
Cosin et al.

(10) Patent No.: US 9,676,811 B2
(45) Date of Patent: Jun. 13, 2017

(54) TESTOSTERONE DERIVATIVES WITH A CARBOXYALKYL SUBSTITUTION IN POSITION 3 AND USE THEREOF FOR THE PRODUCTION OF LABELLED STEROIDS FOR DETERMINING THE CONCENTRATION OF TESTOSTERONE IN A BIOLOGICAL SAMPLE

(71) Applicant: BIOMERIEUX, Mercy l'Etoile (FR)

(72) Inventors: Perrine Cosin, Sainte-Consorce (FR); Yuping Guo, Tarare (FR)

(73) Assignee: BIOMERIEX, Marcy l'Etoile (FR)

( * ) Notice: Subject to any disclaimer, the term of this patent is extended or adjusted under 35 U.S.C. 154(b) by 0 days.

(21) Appl. No.: 14/649,355

(22) PCT Filed: Dec. 12, 2013

(86) PCT No.: PCT/FR2013/053040
§ 371 (c)(1),
(2) Date: Jun. 3, 2015

(87) PCT Pub. No.: WO2014/091158
PCT Pub. Date: Jun. 19, 2014

(65) Prior Publication Data
US 2015/0299244 A1 Oct. 22, 2015

(30) Foreign Application Priority Data
Dec. 13, 2012 (FR) ..................... 12 61982

(51) Int. Cl.
| G01N 33/74 | (2006.01) |
|---|---|
| C07J 41/00 | (2006.01) |
| C07J 43/00 | (2006.01) |
| C07J 1/00 | (2006.01) |
| C07J 51/00 | (2006.01) |

(52) U.S. Cl.
CPC ......... *C07J 1/0022* (2013.01); *C07J 41/0038* (2013.01); *C07J 43/003* (2013.01); *C07J 51/00* (2013.01); *G01N 33/74* (2013.01)

(58) Field of Classification Search
CPC ...... C07J 1/0022; C07J 41/0038; C07J 51/00; C07J 43/003; G01N 33/74
See application file for complete search history.

(56) References Cited

FOREIGN PATENT DOCUMENTS
WO  95/08000 A2  3/1995

OTHER PUBLICATIONS

Tuomola et al. Production and characterisation of monoclonal antibodies agaist a very small hapten, 3-methylindole. J. Immunol. Methods. 2000, vol. 240, pp. 111-124.*

Cook, Brian et al., "Measurement of Steroid Hormone Concentrations in Blood, Urine and Tissues," 1987.
Moneti, G. et al., "Determination of Testosterone and its Tissue Metabolites (DHT and 3alpha-DIOL) in Human Plasma and Prostatic Tissue by Isotopic Dilution Mass Spectrometry," Journal of Steroid Biochemistry, vol. 27, No. 1-3, (1987), pp. 53-59.
Cekan, S.Z., "On the Assessment of Validity of Steroid Radioimmunoassays," Journal of Steroid Biochemistry, vol. 11, (1979), pp. 1629-1634.
Vingler, Phillipe et al., "Direct Quantitative Digital Autoradiography-thin-layer Chromatography of 3alpha,3beta- and 5alpha-reduced and 17beta-dehydrogenated Androgens Derived from Testosterone Metabolism," Journal of Chromatography, vol. 571, (1991), pp. 73-86.
Rassaie, Mohammad J. et al., "Influence of Different Combinations of Antibodies and Penicillinase-labeled Testosterone Derivatives on Sensitivity and Specificity of Immunoassays," Steroids, vol. 57, Mar. 1992, pp. 112-118.
Wudy, Stefan A. et al., "Androgen Metabolism Assessment by Routine Gas Chromatography/Mass Spectrometry Profiling of Plasma Steroids: Part 1, Unconjugated Steroids," Steroids, vol. 57, Jul. 1992, pp. 319-324.
Thienpont, Linda M. et al., "State-of-the-Art of Serum Testosterone Measurement by Isotope Dilution—Liquid Chromatography—Tandem Mass Spectrometry," Clinical Chemistry, vol. 54, No. 8, (2008), pp. 1290-1297.
Ueshiba, Hajime et al., "Serum Profiles of Steroid Hormones in Patients with Cushing's Syndrome Determined by a New HPLC/RIA Method," Clinical Chemistry, vol. 37, No. 8, (1991), pp. 1329-1333.
Stabler, T.V. et al., "Chemiluminescence Immunoassay of Aldosterone in Serum," Clinical Chemistry, vol. 37, No. 11, (1991), pp. 1987-1989.
Rosner, William et al., "Position Statement: Utility, Limitations, and Pitfalls in Measuring Testosterone: An Endocrine Society Position Statement," The Journal of Clinical Endocrinology & Metabolism, vol. 92, No. 2, (2007), pp. 405-413.
Owen, William E. et al., "Selected Performance Characteristics of the Roche Elecsys® Testosterone II Assay on the Modular Analytics E 170 Analyzer," Clinica Chemica Acta, vol. 411, (2010), pp. 1073-1079.
Fiet, Jean et al., "Development of a Highly Sensitive and Specific New Testosterone Time-Resolved Fluoroimmunoassay in Human Serum," Steroids, vol. 69, (2004), pp. 461-471.

(Continued)

*Primary Examiner* — Shafiqul Haq
(74) *Attorney, Agent, or Firm* — Oliff PLC

(57) ABSTRACT

A testosterone derivative of formula (I):

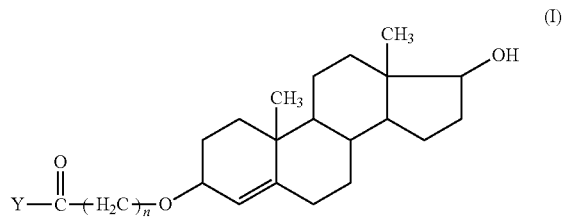

Figure 1:
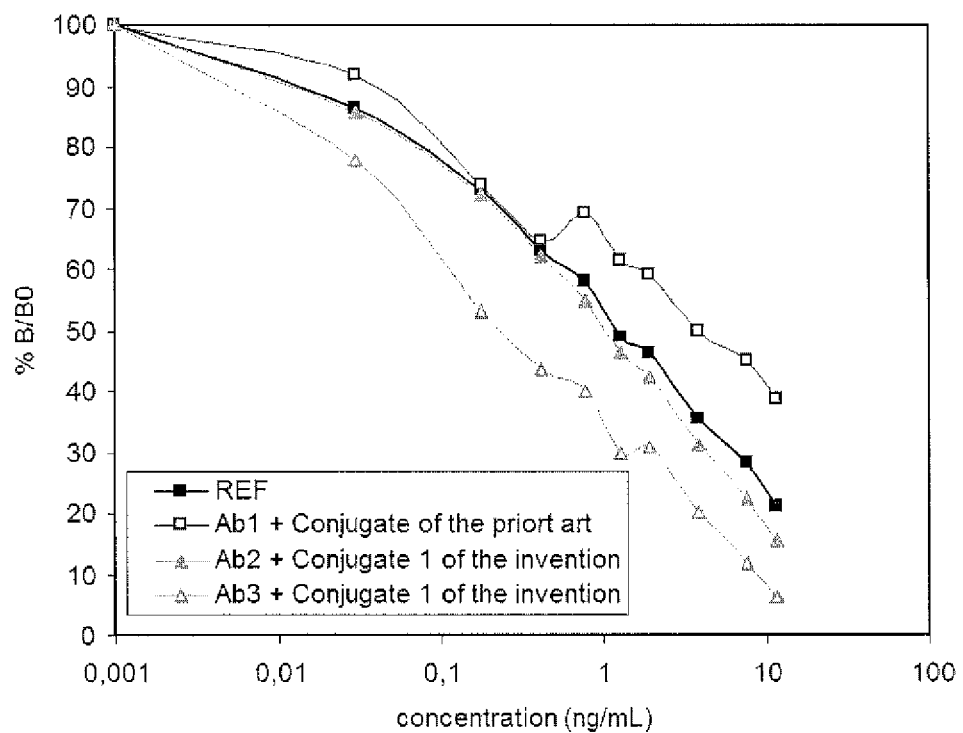

where n is an integer in a range of from 1 to 10, and Y represents an activated or ready-to-be-activated group allowing formation of an amide bond with a primary amine of a molecule. Conjugates including the testosterone derivatives and a marker, methods for determining the concentration of testosterone in a biological sample, and methods for preparing the testosterone derivatives are also provided.

21 Claims, 2 Drawing Sheets

(56) References Cited

OTHER PUBLICATIONS

Rajkowski, K.M. et al., "The Conjugation of Testosterone with Horseradish Peroxidase and a Sensitive Enzyme Assay for the Conjugate," Steroids, vol. 29, No. 5, May 1 1977, pp. 701-713.
Dhar, Tarun K. et al., "Homogeneous Enzyme Immunoassay of Estradiol Using Estradiol-3-O-Carboxymethyl Ether as Hapten," Steroids, vol. 51, No. 5-6, May 1, 1988, pp. 519-526.
Fiet, Jean et al., "Plasma 17-OH Pregnenolone: Comparison of a Time-Resolved Fluoroimmunoassay using a New Tracer 17-OH Pregnenolone-3-Oxyacetyl-Biotine with a Radioimmunoassay using 125I 17-OH Pregnenolone-3-Hemisuccinate-Histamine," Steroids, vol. 66, (2001), pp. 81-86.
Mar. 4, 2014 Written Opinion issued in International Patent Application No. PCT/FR2013/053040.
Mar. 4, 2014 Search Report isssued in International Patent Application No. PCT/FR2013/053040.
Demers, Laurence M., "Androgen Deficiency in Women; Role of Accurate Testosterone Measurements," Maturitas, vol. 67, (2010), pp. 39-45.
Textbook of Biochemistry with Clinical Correlations, Fourth Edition, pp. 901-925, 1997.
Wong, "Chemistry of Protein Conjugation and Cross-linking," pp. 33-39, 1991.

\* cited by examiner

TESTOSTERONE DERIVATIVES WITH A CARBOXYALKYL SUBSTITUTION IN POSITION 3 AND USE THEREOF FOR THE PRODUCTION OF LABELLED STEROIDS FOR DETERMINING THE CONCENTRATION OF TESTOSTERONE IN A BIOLOGICAL SAMPLE

The present invention relates to the field of the detection of testosterone in a biological sample. In particular, it relates to novel compounds derived from testosterone that are particularly useful in immunoassays, the method of preparation thereof, as well as the use thereof for determining testosterone.

The androgen 17β-hydroxyandrost-4-en-3-one, commonly called testosterone, is the main androgen hormone in humans. It is secreted by the Leydig cells in the testes, under the influence of a pituitary hormone: LH (luteinizing hormone).

Testosterone circulates largely bound to transport proteins, mainly SHBG (Sex Hormone-Binding Globulin) and albumin. Free testosterone represents 1 to 2% of total testosterone (Litwack G., 1992).

The structural formula of testosterone with the numbering of the atoms is shown below.

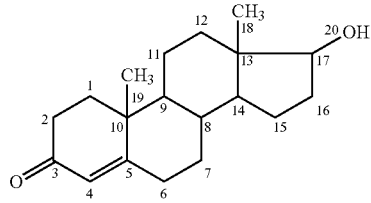

In humans, testosterone acts on spermatogenesis, on maturation of the external genital organs, on secondary sex characteristics (beard, pubic and axillary hair) and on protein anabolism. Thus, determination of testosterone in humans makes it possible to evaluate testicular steroidogenic function. A serum testosterone level above 3.2 ng/ml is regarded as normal, a level below 2 ng/ml allows a diagnosis of hypogonadism or feminization of the body. The upper limit of the normal values in humans is 8-9 ng/ml.

In women, testosterone is secreted in small amounts by the ovaries and the adrenal glands. It arises essentially from the peripheral conversion of precursors (notably androstenedione). Thus, determination of testosterone in women allows exploration of androgen secretion. High levels of testosterone may be associated with polycystic ovarian syndrome, an ovarian or adrenal tumor, hyperplasia of the adrenal glands or idiopathic hirsutism.

Several methods are available for quantifying testosterone in biological samples. These methods may be classified in 2 main groups:

(1) mass spectrometry (MS)

This analytical technique allows determination of the molecular weight of the compounds analyzed, and as well as identification and quantification of them. Applied to a complex mixture like a biological fluid, it needs to be coupled to a separation technique that allows its complexity to be reduced. Most often this is gas chromatography (GC) or liquid chromatography (LC). Tandem mass spectrometry (MS/MS) combines 2 analyzers. The ionic compounds selected in the first analyzer are analyzed more finely in the second analyzer. This double analysis makes it possible to significantly increase the specificity of the method. Thus, testosterone may be determined by several methods that combine a separation technique and an MS technique:

- gas chromatography—mass spectrometry with isotope dilution (ID-GCMS) (Moneti G., et al., 1987; Wudy, S. A., et al., 1992).
- liquid chromatography tandem mass spectrometry with isotope dilution (ID-LC-MS/MS) (Thienpont L., et al., 2008).

(2) immunoassays with markers

The immunoassay methods, also called immunologic assays or immunochemical assays, involve immunologic reactions between the analyte to be detected, testosterone, and at least one first compound that is a binding partner to this analyte. As testosterone assay is performed by competition, the method also involves another compound that competes with the testosterone to be determined, and is a testosterone derivative. One of the two compounds will then be labeled for visualization. This labeled compound will be called a labeled conjugate.

Of course, the term "immuno", in "immunoassay" for example, is not to be regarded in the present application as strictly indicating that the binding partner is an immunologic partner, such as an antibody. In fact, this term is also used widely by persons skilled in the art when the binding partner, also called ligand, is not an immunologic partner but is for example a receptor for the analyte that is to be determined. Thus, the term ELISA (Enzyme-Linked Immunosorbent Assay) tends to be used for assays that use nonimmunologic binding partners, more generally called "Ligand Binding Assay" in English, whereas the term "immuno" is included in the acronym ELISA. For clarity, the applicant will use the term "immuno" throughout this application for any assay using a binding partner, even when it is not an immunologic partner.

According to the type of labeled conjugate that is used and the type of signal that this conjugate may generate, a distinction is made between three types of immunoassay:

- radioisotope immunoassays (RIA) (Cekan, S. Z., 1979), which may be preceded by a separation technique such as high-performance liquid chromatography (Ueschiba, H. et al., 1991),
- immuno-enzymatic assays or EIA "enzyme linked immunoassay". Depending on the enzyme substrate selected, we may have a colorimetric signal (ELISA) (Rassasie, M. J., et al., 1992), a fluorescence signal (ELFA) or a chemiluminescent signal (CLIA) (Stabler T. V., et al., 1991).
- electrochemiluminescent immunoassays (Owen, W. E., et al., 2010).

The last two types of immunoassay are then called non-radioisotopic immunoassays.

Development of RIA methods in the 1960s revolutionized quantification of the steroids. The tracers used at that time were radioactive testosterone derivatives ($^3$H or $^{125}$I) such as labeled testosterone-3-(O-earboxymethyl)oxime (or testosterone-3-O-CMO) (Cook B. and Beastall G. H., 1987). However, these methods had the notable drawbacks of treatment of radioactive waste and relatively short half-life of the labeled reagents.

That is why the methods and reagents of non-radioisotopic immunoassay developed to the detriment of RIA, which is only rarely used today. However, immunoassays carried out on automated irxmlunoanalysis platforms are not capable of correctly and reproducibly detecting amounts of testosterone below 1.5 ng/ml in the conditions of routine use (Rosner W. et al., 2007). This poses a problem for the proper management of people with hypogonadism, who often have serum levels this low.

Moreover, it has also been established that most of the existing methods of non-radioisotopic immunoassay of testosterone are inaccurate when they are used in women as they do not possess sufficient analytical sensitivity to detect and quantify the levels of testosterone present in the blood circulation. The reference values for total testosterone in women in the age range from 18 to 49 years are from 0.04 to 0.44 ng/ml (Demers L. M., 2010), whereas the limits of detection or analytical sensitivity of the automated immunoassays for testosterone are of the order of 0.1 ng/ml. Thus, Shrivastav T. G., 2002 showed that determination of testosterone by ELISA using, as tracer, testosterone-3-O-CMO conjugated with horseradish peroxidase gave a bias when the amount of testosterone in the sample to be assayed was low, in the sense that the concentration obtained was always well above that actually contained in the sample assayed. Fiet J. et al., 2004 also described the use of such a compound 3-O-CMO, also called compound 3-CMO, as tracer, which was biotinylated beforehand. However, the sensitivity of determination of testosterone in the lowest ranges using this compound is not good. Moreover, said compound 3-O-CMO is complicated to produce, in that it is in the form of a mixture of stereoisomers, also called isomer mixture. For a reproducible assay, it is then recommended to separate the stereoisomers prior to use in immunoassay, which is complicated and leads to degradation of the synthesis yield.

There is therefore an urgent need for an assay for testosterone that is sufficiently sensitive and therefore clinically usable in samples containing a low testosterone concentration and using compounds that can be prepared easily.

Against all expectations, the applicant has found novel testosterone derivatives that make it possible to overcome the drawbacks of the immunoassays of the prior art in the sense that the use thereof in a competitive immunoassay, notably as tracer, provides a highly sensitive assay, in particular in the lowest ranges of testosterone, and with easy preparation.

Thus, one object of the invention relates to compounds derived from testosterone of the following general formula (I):

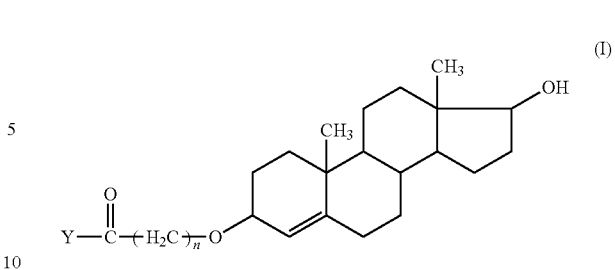

in which n is an integer between 1 and 10 and Y represents an activated or ready-to-be-activated coupling group allowing formation of an amide bond with a primary amine of a molecule.

Another object of the invention comprises a conjugate comprising or consisting of a testosterone derivative of formula (I) as described above and a marker, as well as a kit comprising said compounds.

Another object of the invention comprises the use of said conjugate in a method of immunoassay of testosterone, notably as a tracer.

Finally, a last object relates to a method for preparing said testosterone derivatives.

The present invention therefore relates to the compounds of formula (I) as described above, which are particularly useful for a competitive immunoassay, and notably for tracer preparation.

Indeed, the applicant found, against all expectations, that modification of testosterone in position 3, by reduction of the carbonyl to hydroxyl and introduction of a linker, gave a testosterone derivative that was not in the form of an isomer mixture and was particularly advantageous when used in an assay for testosterone, and notably as a tracer, in the sense that the determination of testosterone is particularly sensitive and makes it possible to detect low testosterone concentrations.

As shown by Cook B. and Beastall G. H., 1987, the steroid hormones are very similar structurally. Thus, testosterone, estradiol, estrone and androstenedione only differ from one another by the presence of a hydroxyl or ketone function in positions 3 and 17, as well as by the presence or absence of a methyl group in position 10, as shown below:

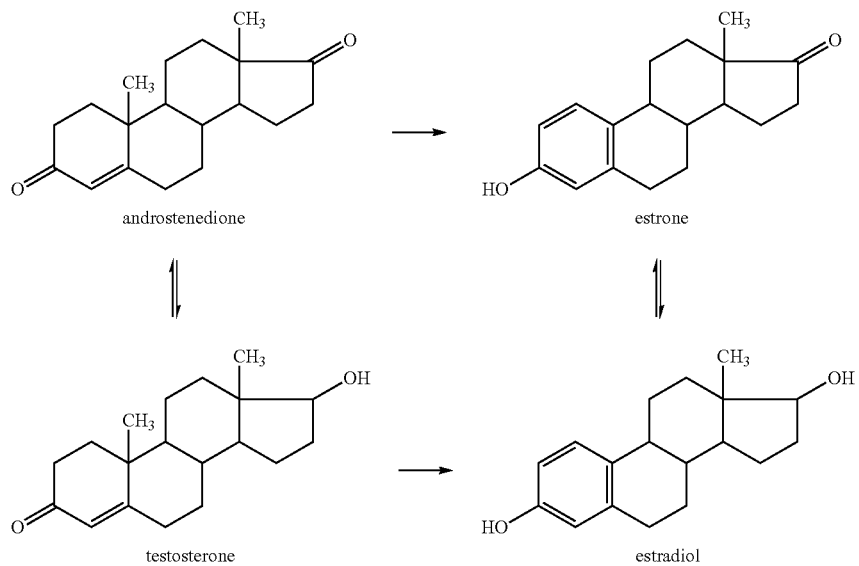 [SMILES: CC12CCC3C(CCC4=CC(=O)CCC43C)C1CCC2=O ; CC12CCC3c4ccc(O)cc4CCC3C1CCC2=O ; CC12CCC(=O)C=C1CCC1C2CCC2(C)C(O)CCC12 ; CC12CCC3c4ccc(O)cc4CCC3C1CCC2O]

The slightest modification of the substituents of the basic structure, and notably in position 3 or position 17, results in the transition from one steroid hormone to another.

Against all expectations, the compounds of formula (I) of the invention, despite modification of the basic chemical structure of testosterone, owing to reduction of the carbonyl to hydroxyl in position 3 and therefore owing to its structural similarity, at the functional group in this position, with estradiol, an analyte that we do not wish to determine, are particularly suitable for use for determining testosterone.

The compounds of the invention are therefore characterized by formula (I) as given above, in which n is an integer between 1 and 10 and Y represents an activated or ready-to-be-activated coupling group allowing formation of an amide bond with a primary amine of a molecule.

These compounds must not be too hydrophobic and the value of n must be controlled in this respect. According to one embodiment, n is between 1 and 5 and preferably between 1 and 3. According to a particular embodiment, n is 1.

The molecules that may be coupled with the testosterone derivatives of the invention are all molecules that naturally possess a primary amine, such as a protein, or else all molecules that have been modified chemically to include such a primary amine, for example a modified biotin, having a primary amine.

"Activated or ready-to-be-activated coupling group" means a suitable functional group that allows, if necessary after activation, coupling of the testosterone derivative of the invention with the primary amine functional group of the coupling molecule. This group may also be called a leaving group, as it will no longer exist in the conjugate formed between the testosterone derivative and the molecule with a primary amine. This leaving group will thus be dissociated from the rest of the molecule during the reaction of nucleophilic substitution with the primary amine nucleophilic group of the coupling molecule of interest. The leaving group will be dissociated directly when it is called "already activated", or it will only be dissociated after activation when it is called "ready-to-be-activated".

"Activated coupling group" therefore means a group that makes it possible to form an amide bond directly, without this group needing to be modified. As an example, we may mention the following groups:

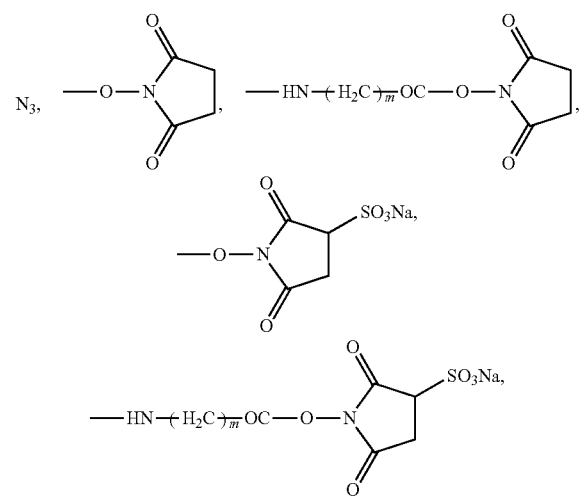

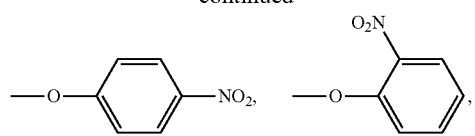

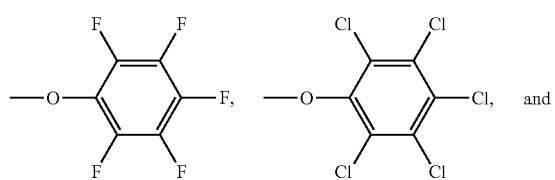

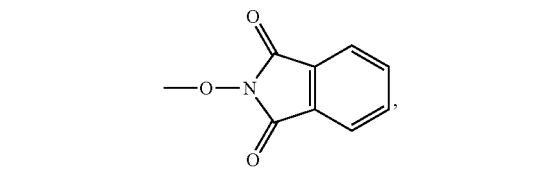

m being an integer, preferably between 1 and 10, which constitutes one embodiment of the invention.

"Ready-to-be-activated coupling group" therefore means any group that has to be activated, by methods known by a person skilled in the art, in order to be capable of forming an amide bond. Such groups possess an OH or COOH group. As examples, we may mention the groups —OH and —NH—(CH$_2$)$_m$—COOH, m being an integer, preferably between 1 and 10, which constitutes one embodiment of the invention.

According to a particular embodiment of the invention, m is between 1 and 5, or else between 1 and 3.

According to another embodiment, Y is selected from —OH, —NH—(CH$_2$)m-COOH, and

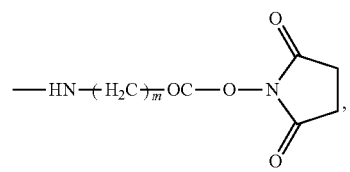

m being between 1 and 10 and preferably being equal to 1.

Compounds that are particularly suitable for determining testosterone, and in particular for tracer preparation, are compounds that are stereochemically pure (α or β isomers) at the carbon in position 3, as there is no longer a double bond in position 3, as in testosterone.

Indeed, in comparison with a 3-O-CMO compound, where it is more difficult to control and reproduce the isomer mixture, as the ratios of the isomers are not identical between synthesis batches, the compounds that are stereochemically pure (α or β isomers) at carbon 3 are advantageous in the sense that they are more reproducible, of better quality, and in that the assays in which they are used are more robust.

The testosterone derivatives of the invention of formula (I) in the form of β isomer in position 3 are represented by the following formula (Iβ):

(Iβ)

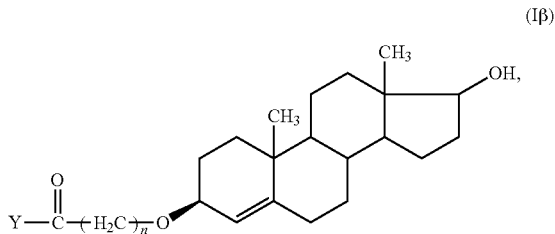

Y and n being as described above.

The testosterone derivatives of the invention of formula (I) in the form of α isomer in position 3 are represented by the following formula (Iα):

(Iα)

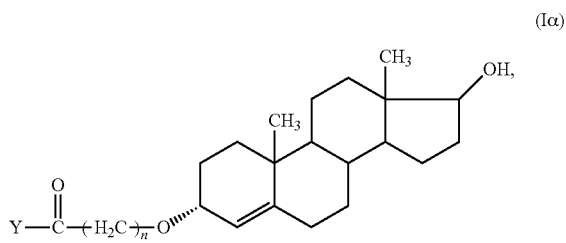

Y and n being as described above

In other words, in formula (I), the bond between the carbon in position 3 and the oxygen atom of the linker, represented in the form of a segment of a straight line as follows: ∕, includes both a bond of the β type and a bond of the α type.

This will also apply to all the compounds described below that comprise a bond, between the carbon in position 3 and the oxygen atom of the linker of said compound, in the form of a segment of a straight line, and not in the form of an arrow as follows: ∕, to denote a β isomer, or ⁓, to denote an α isomer.

This will notably apply to the compounds used in the description of the methods for preparing the testosterone derivatives of the invention, for which the symbol α or β with the numeral denoting the formula is not added.

The compounds of the invention may be used in two ways in the methods of determining testosterone by competitive immunoassay, such as diagnostic tests. Either they are used as they are, or they are used coupled to another molecule to form a conjugate. Said other molecule is either a marker, or a chemical linkage or "linker", or a chemical compound whose coupling with a testosterone derivative is of interest for implementing testosterone assay by competitive immunoassay.

Thus, the present invention also relates to the conjugate comprising or consisting of a testosterone derivative as described above and another molecule, in particular a marker or a chemical linkage.

"Marker" means any molecule containing a primary amine group, directly without chemical modification, or after chemical modification in order to include such a group, said molecule being capable of directly or indirectly generating a detectable signal. A non-exhaustive list of these markers for direct detection consists of:

enzymes that produce a signal that is detectable for example by colorimetry, fluorescence, luminescence, such as horseradish peroxidase, alkaline phosphatase, β-galactosidase, glucose-6-phosphate dehydrogenase, chromophores such as fluorescent compounds, luminescent compounds, dyes, radioactive molecules such as $^{32}P$, $^{35}S$ or $^{125}I$, and fluorescent molecules such as the Alexa or phycocyanins; electrochemiluminescent salts such as organometallic derivatives based on acridinium or ruthenium.

Indirect detection systems may also be used, for example ligands capable of reacting with an anti-ligand. The ligand then corresponds to the marker and constitutes, with the testosterone derivative, the conjugate of the invention.

Ligand/anti-ligand pairs are familiar to a person skilled in the art, as is the case for example for the following pairs: biotin/streptavidin, hapten/antibody, antigen/antibody, peptide/antibody, sugar/lectin, polynucleotide/complementary of the polynucleotide.

The anti-ligand may then be detectable directly by the direct detection markers described above or may itself be detectable by another ligand/anti-ligand pair, and so on.

These indirect detection systems may lead, in certain conditions, to amplification of the signal. This technique for signal amplification is familiar to a person skilled in the art, and reference may be made to the applicant's previous patent applications FR98/10084 or WO-A-95/08000.

Depending on the type of labeling used, a person skilled in the art will add reagents allowing visualization of the labeling or the emission of a signal that is detectable by any suitable type of measuring apparatus, for example a spectrophotometer, a spectrofluorometer, or a high definition camera.

Chemical linkage or "linker" means any molecule containing a primary amine group, directly without chemical modification, or after chemical modification in order to include such a group, said molecule being capable of fixation on a solid phase, covalently or noncovalently, selectively or nonselectively.

As pointed out above, the testosterone derivatives or the conjugates of the invention are particularly useful for in vitro determination of the concentration of testosterone in a biological sample, which constitutes another object of the invention.

The biological sample in which the method of the invention may be carried out is any animal, preferably human, biological sample that may contain testosterone, in which an immunoassay can be performed. These samples are widely known by a person skilled in the art. The samples employed in the assay method may or may not be modified prior to their use. As examples of such samples that are not modified beforehand, we may mention biological fluids such as whole blood, urine, cerebrospinal fluid, seminal fluid, sperm, leukorrhea (vaginal secretions), cervical mucus, cervicovaginal wash, rectal wash, saliva, bronchoalveolar wash and amniotic fluid. As examples of samples modified beforehand, also called sample derivatives, we may mention serum, plasma, the cells that are recovered from a biopsy or following surgery and that are cultured in vitro. The concentration of testosterone may then be determined in the culture supernatant or else in the cellular lysate.

The concentration of testosterone in the biological sample may be determined by a method of competitive immunoassay, also called immunologic assay, which comprises the steps consisting of:

a) bringing into contact, within said sample, (i) a testosterone binding partner and (ii) a compound selected from a testosterone derivative and a conjugate as described above, one of said components (i) and (ii) being adapted to emit a signal, b) optionally waiting a sufficient time to allow the competition reaction and c) measuring the intensity of the signal and deducing from that the concentration of testosterone present in said biological sample by comparing with a calibration curve establishing a relationship between the measured signal intensity and the testosterone concentration.

Competitive immunoassay is an assay that is widely known by a person skilled in the art. It consists of determining the analyte, in this case testosterone, in the sample, by creating competition between the analyte of the sample and a derivative of said analyte, in this case the testosterone derivative. The immunologic reaction is then detected owing to the presence of a tracer.

The derivative of the analyte may be used in the competition reaction, as pointed out above, without prior coupling or after coupling to a marker to form a conjugate or tracer.

The immunoassay also requires the use of a testosterone binding partner, in respect of which the analyte derivative and the analyte compete. When the analyte derivative is not coupled to a marker (it is not the tracer but the capture partner), the binding partner is then labeled to constitute the tracer of the reaction. When the analyte derivative is coupled to a marker (it is then the tracer), the binding partner then becomes the capture partner.

The measured signal emitted by the tracer is then inversely proportional to the amount of testosterone in the sample.

"Testosterone binding partner" means any molecule capable of binding to testosterone. As examples of testosterone binding partners, we may mention antibodies, antibody fractions, Nanofitins, testosterone receptors or any other protein that is known to have an interaction with testosterone, for example SHBG.

The antibodies as binding partners are for example either polyclonal antibodies, or monoclonal antibodies.

The polyclonal antibodies may be obtained by immunization of an animal with the target testosterone as immunogen, followed by recovery of the required antibodies in purified form, by taking serum from said animal, and separating said antibody from the other constituents of the serum, notably by affinity chromatography on a column on which an antigen is fixed that is specifically recognized by the antibodies, notably the immunogen.

The monoclonal antibodies may be obtained by the hybridoma technique that is widely known by a person skilled in the art. The monoclonal antibodies may also be recombinant antibodies obtained by genetic engineering, by techniques familiar to a person skilled in the art.

As examples of antibody fragments, we may mention the fragments Fab, Fab', F(ab')$_2$ as well as the chains scFv (single chain variable fragment), dsFv (double-stranded variable fragment). These functional fragments may notably be obtained by genetic engineering.

The Nanofitins (trade name) are small proteins which, like the antibodies, are capable of binding to a biological target, thus making it possible to detect it, capture it or quite simply target it within an organism.

The binding partners used may or may not be specific to testosterone. They are said to be specific when they are capable of binding exclusively or almost exclusively to testosterone. They are said to be nonspecific when the testosterone binding selectivity is low and they are then capable of binding to other ligands, such as other proteins or antibodies. According to a preferred embodiment, the specific binding partners are preferred.

The binding partners or the testosterone derivatives, when they are used in capture, may or may not be bound to a substrate by any technique widely known by a person skilled in the art.

The second step b) of the method of the invention is a conventional step of a method of competitive assay.

The last step c) of the method of the invention consists of determining the testosterone concentration. As noted above, the measured signal is inversely proportional to the amount of testosterone in the sample. To determine the concentration, the signal is compared with a calibration curve obtained beforehand by techniques widely known by a person skilled in the art. Thus, for example, the calibration curve is obtained by performing an immunoassay using the same binding partner as well as increasing amounts of testosterone. A curve is thus obtained by plotting the testosterone concentration on the abscissa and the corresponding signal obtained after immunoassay on the ordinate.

When compound (ii) is a conjugate of the invention as described above, which constitutes one embodiment of the invention, the signal is obtained via the labeling with the marker as described above.

When compound (ii) is a testosterone derivative of the invention as described above, i.e. it is not bound to a marker, the signal consists of direct reading of the binding of the binding partner/testosterone derivative, which may be done for example by surface plasmon resonance or by cyclic voltammetry.

For carrying out the method of determination of the testosterone concentration, the testosterone derivatives or conjugates of the invention as described above are incorporated in a diagnostic kit, which constitutes another object of the invention. Of course, the kit may comprise other constituents necessary for performing the immunoassay, such as, for example, at least one binding partner, a calibration means, washing buffers and reagents allowing visualization of the labeling or emission of a detectable signal.

The testosterone derivatives were prepared by particular methods for synthesizing compounds which are either pure isomers α, or pure isomers β. These methods are novel and constitute another object of the invention.

The methods for preparing all the testosterone derivatives of the invention of formula (I) include the preparation of a first key compound, which is a compound of formula (Ia) as follows:

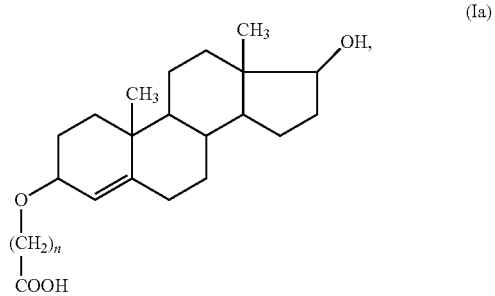

in which n is as defined above. Thus, its use for preparing a compound of formula (I) as defined above constitutes another object of the invention.

The compound of formula (Ia) is in fact a testosterone derivative of formula (I) in which Y is the OH group. This testosterone derivative may be in the form of β isomer in position 3; it then has the following formula (Iaβ):

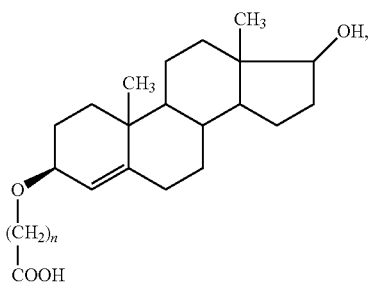

n being as defined above.

Thus, another object of the invention consists of a method for preparing a testosterone derivative, in the form of β isomer in position 3, of the following general formula (Iaβ), which comprises or consists of the steps consisting of:
(1) reacting testosterone with acetic anhydride to protect the OH function of position 17, and then with a reducing agent, in the presence of a solvent, to reduce the carbonyl in position 3 and obtain the compound of formula (IIβ):

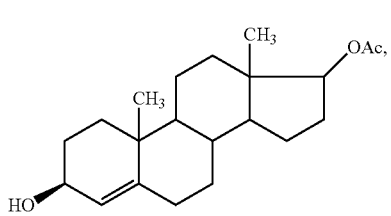

in which Ac means —CO—CH$_3$,
(2) reacting the compound of formula (IIβ) thus obtained with the compound of formula (III): N$_2$CH—(CH$_2$)$_{n-1}$—COOC$_2$H$_5$, and then reacting with a base, in the presence of a solvent, to obtain the compound of formula (Iaβ).

The testosterone derivative of formula (I) in which Y is —OH may also be in the form of an α isomer in position 3; it then has the following formula (Iaα):

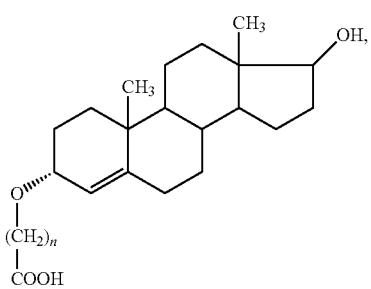

in which n is as described above.

Yet another object of the invention relates to a method for preparing a testosterone derivative, in the form of an α isomer in position 3, of the following general formula (Iaα), said method comprising or consisting of the steps consisting of:

(1) reacting testosterone with t-butyldimethylchlorosilane to protect the OH function of position 17, and then with a reducing agent, in the presence of a solvent, to reduce the carbonyl 3 and obtain the compound of formula (VIIIβ):

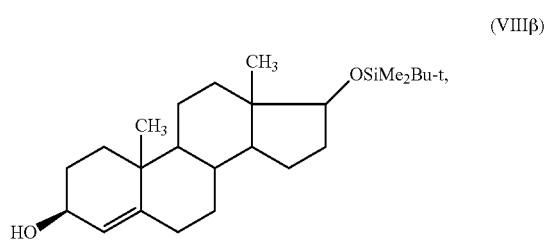

in which —SiMe$_2$Bu-t means t-butyldimethylsilanyl,
(2) reacting the compound of formula (VIIIβ) thus obtained with triphenylphosphine, benzoic acid and diethyl azodicarboxylate, and then with a base, in the presence of a solvent, to transform, in position 3, the β isomer to a isomer and thus obtain the compound of formula (VIIIα):

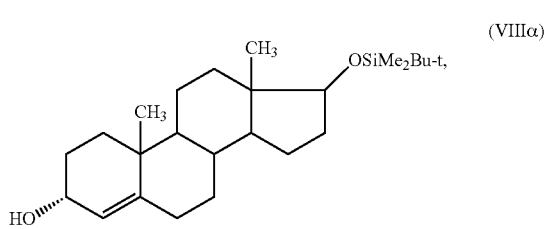

in which —SiMe$_2$Bu-t means t-butyldimethylsilanyl, and
(3) reacting the compound of formula (VIIIα) thus obtained with the compound of formula (III): N$_2$CH—(CH$_2$)$_{n-1}$—COOC$_2$H$_5$, and then reacting with a base, in the presence of a solvent, to obtain the compound of formula (Ian).

The reducing agents that may be used here are any reducing agent known by a person skilled in the art for reducing a carbonyl to hydroxyl stereoselectively. As an example, we may mention sodium borohydride.

The solvents that may be used here are any solvents that make it possible to have a reaction that inverts the stereochemistry of the hydroxyl. As an example, we may mention alcohols such as methanol and ethanol.

The bases that may be used here are any mineral bases that allow saponification for return to an —OH group. As an example, we may mention sodium hydroxide and potassium hydroxide.

As noted above, the compounds of formula (Iaβ) or (Iaα) are key for preparing other testosterone derivatives of the invention. Thus, for example, in formula (I), when Y represents —NH—(CH$_2$)m-COOH, the testosterone derivatives then being compounds of the following formulas (Ibβ) or (Ibα) depending on whether they are respectively β or a isomers in position 3:

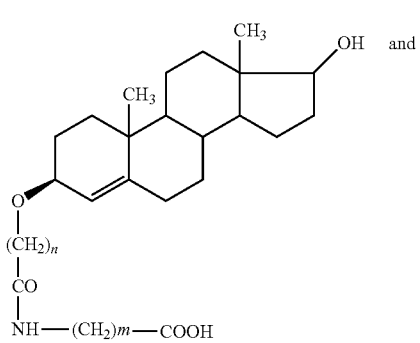

(Ibβ)

and

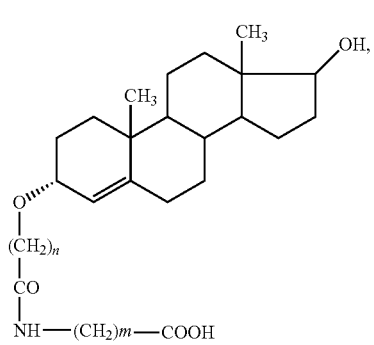

(Ibα)

n and m being as defined above, the methods of preparation comprise the preceding steps (1) and (2) for the β isomers and (1) to (3) for the α isomers, as well as the following 3 steps:

1. reacting the compound of formula (Iaβ) or (Iaα) thus obtained with N-hydroxysuccinimide, in the presence of a carbodiimide derivative, to produce the compound of formula (IV):

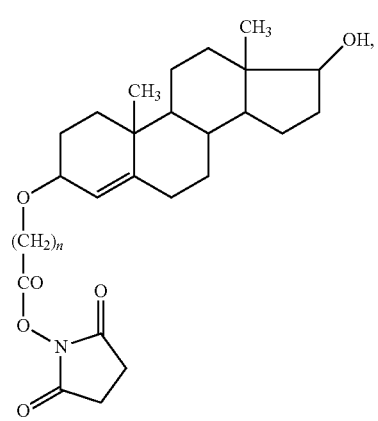

(IV)

2. reacting the compound of formula (IV) thus obtained with the compound of formula (V): $H_2N-(CH_2)m-COOR_1$, in which $R_1$ is an alkyl or aryl group, to produce the compound of formula (VI):

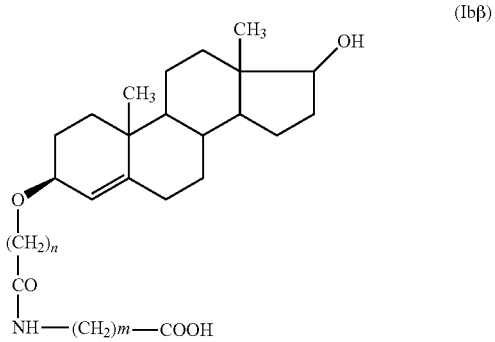

(VI)

3. reacting the compound of formula (VI) thus obtained with a base, in the presence of a solvent, to obtain the compound of formula (Ibβ) or (Ibα).

Thus, according to another object, the invention comprises a method for preparing a testosterone derivative, in the form of β isomer in position 3, of the following general formula (Ibβ):

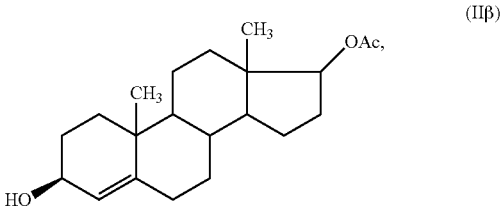

(Ibβ)

in which n is an integer between 1 and 10, m is an integer between 1 and 10, comprising or consisting of the steps consisting of:

(1) reacting testosterone with acetic anhydride to protect the OH function of position 17, and then with a reducing agent, in the presence of a solvent, to reduce the carbonyl in position 3 and obtain the compound of formula (IIβ):

(IIβ)

in which Ac means $-CO-CH_3$, (2) reacting the compound of formula (IIβ) thus obtained with the compound of formula (III): $N_2CH-(CH_2)_{n-1}-COOC_2H_5$, and then reacting with a base, in the presence of a solvent, to obtain the compound of formula (Iaβ):

(Iaβ)

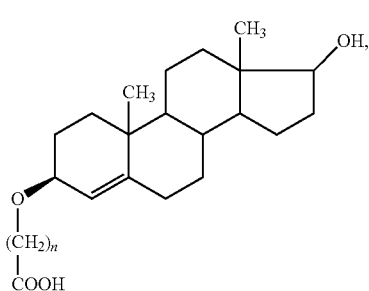

(Ibα)

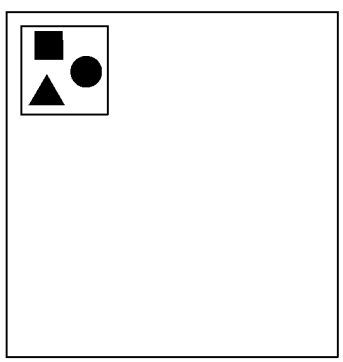

in which n is an integer between 1 and 10, m is an integer between 1 and 10, comprising or consisting of the steps consisting of:

(3) reacting the compound of formula (Iaβ) thus obtained with N-hydroxysuccinimide, in the presence of a carbodiimide derivative, to produce the compound of formula (IVβ):

(IVβ)

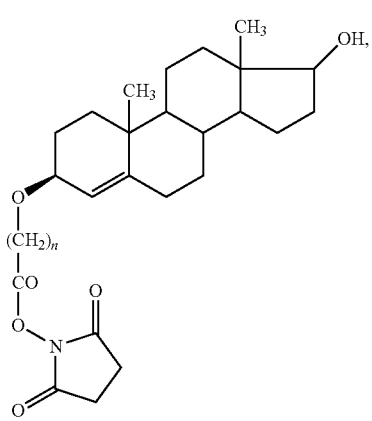

(4) reacting the compound of formula (IVβ) thus obtained with the compound of formula (V): $H_2N-(CH_2)_m-COOR_1$, in which $R_1$ is an alkyl or aryl group, to produce the compound of formula (VIβ):

(VIβ)

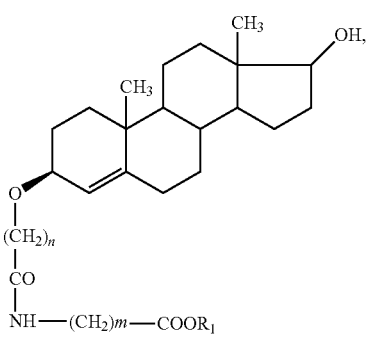

(5) reacting the compound of formula (VIβ) thus obtained with a base, in the presence of a solvent, to obtain the compound of formula (Ibβ).

According to yet another object, the invention comprises a method for preparing a testosterone derivative, in the form of a isomer in position 3, of the following general formula (Ibα):

(1) reacting testosterone with t-butyldimethylchlorosilane to protect the OH function of position 17, and then with a reducing agent, in the presence of a solvent, to reduce the carbonyl in position 3 and obtain the compound of formula (VIIIβ):

(VIIIβ)

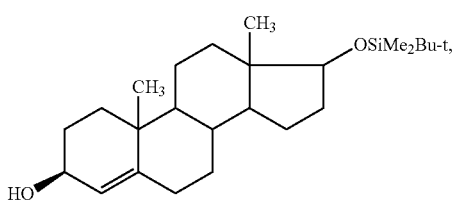

in which —SiMe₂Bu-t means t-butyldimethylsilanyl, (2) reacting the compound of formula (VIIIβ) thus obtained with triphenylphosphine, benzoic acid and diethyl azodicarboxylate, and then with a base, in the presence of a solvent, to transform, in position 3, the β isomer to a isomer and thus obtain the compound of formula (VIIIα):

(VIIIα)

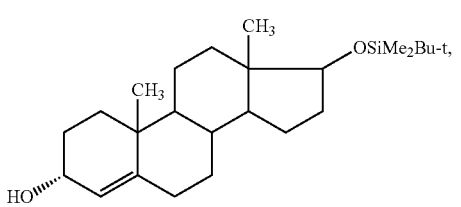

in which —SiMe₂Bu-t means t-butyldimethylsilanyl, (3) reacting the compound of formula (VIIIα) thus obtained with the compound of formula (III): $N_2CH-(CH_2)_{n-1}-COOC_2H_5$, and then reacting with a base, in the presence of a solvent, to obtain the compound of formula (Iaα):

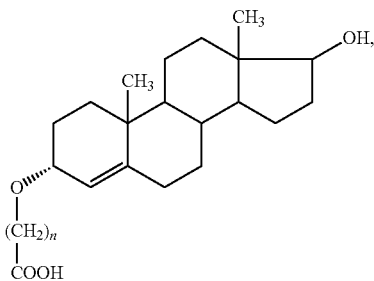

(Iaα)

(4) reacting the compound of formula (Iaα) thus obtained with N-hydroxysuccinimide, in the presence of a carbodiimide derivative, to produce the compound of formula (IVα):

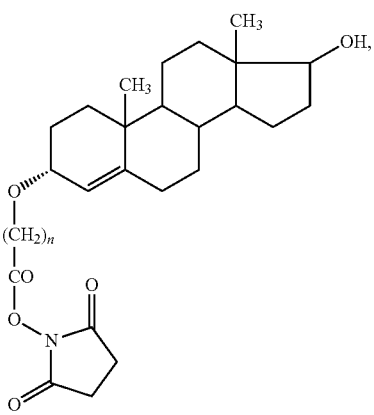

(IVα)

(5) reacting the compound of formula (IVα) thus obtained with the compound of formula (V): $H_2N-(CH_2)m-COOR_1$, in which $R_1$ is an alkyl or aryl group, to produce the compound of formula (VIα):

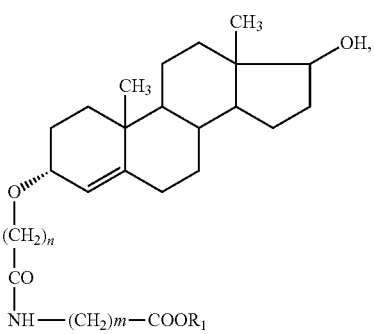

(VIα)

(6) reacting the compound of formula (VIα) thus obtained with a base, in the presence of a solvent, to obtain the compound of formula (Ibα). The bases and solvents used in the additional steps are as stated above.

N-hydroxysuccinimide, of formula

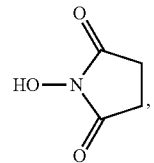

which, when it loses its hydrogen at the hydroxyl group, becomes an activated group Y, allows activation, to activated group, of the ready-to-be-activated group Y=—OH of the compound of formula (Ia), in the presence of a derivative of carbodiimide. The latter may be for example dicyclohexylcarbodiimide or 1-ethyl-3-(3-dimethyl-aminopropyl)carbodiimide.

The alkyls and the aryls are groups that are known by a person skilled in the art. As nonlimiting examples of alkyl group, we may mention methyl, ethyl, propyl, isopropyl, butyl, t-butyl, pentyl. As nonlimiting examples of aryl group, we may mention phenyl, benzyl, tolyl, xylyl, benzylidene, benzoyl and naphthyl.

When Y represents one of the following groups:

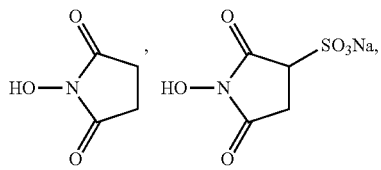

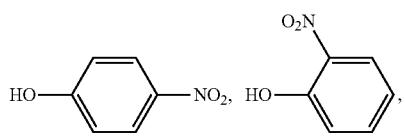

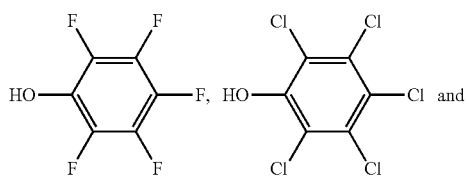

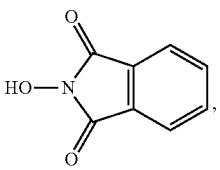

the testosterone derivatives then being compounds of the following formula (Iβ) or (Iα) depending on whether they are respectively β or α isomers in position 3:

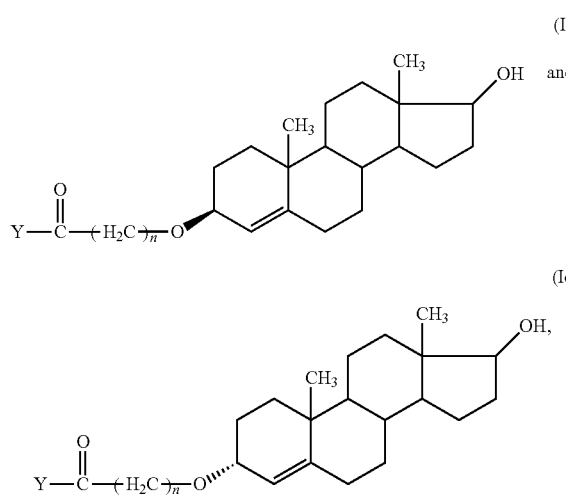

n being as defined above, the methods of preparation comprise the preceding steps (1) and (2) for the β isomers and (1) to (3) for the α isomers, as well as the following step:

1. reacting the compound of formula (Iaβ) or (Iaα) thus obtained, in the presence of a carbodiimide derivative, with a reagent selected, depending on the final group Y, from the following compounds, to obtain the compounds of formula (Iβ) or (Iα):

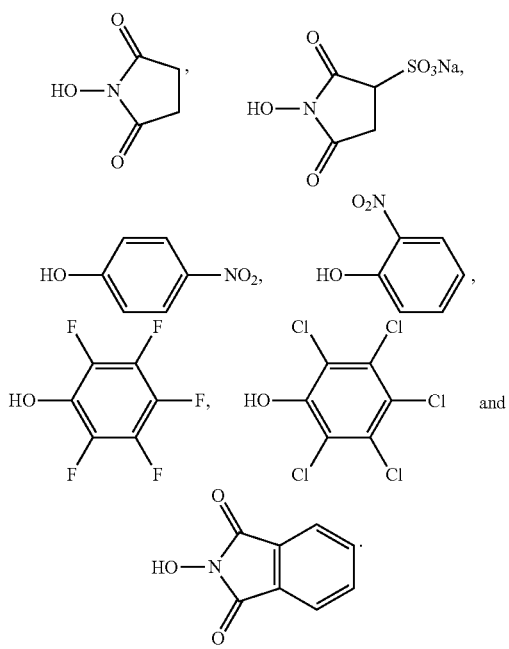

Once again, activation of the ready-to-be-activated group of compound (Ia), Y=—OH, is carried out using, in the presence of a carbodiimide derivative, one of the appropriate seven compounds above which, when they lose the hydrogen of the hydroxyl group, become activated groups Y.

Thus, the invention further relates to a method for preparing a testosterone derivative, in the form of β isomer in position 3, of the following general formula (Iβ):

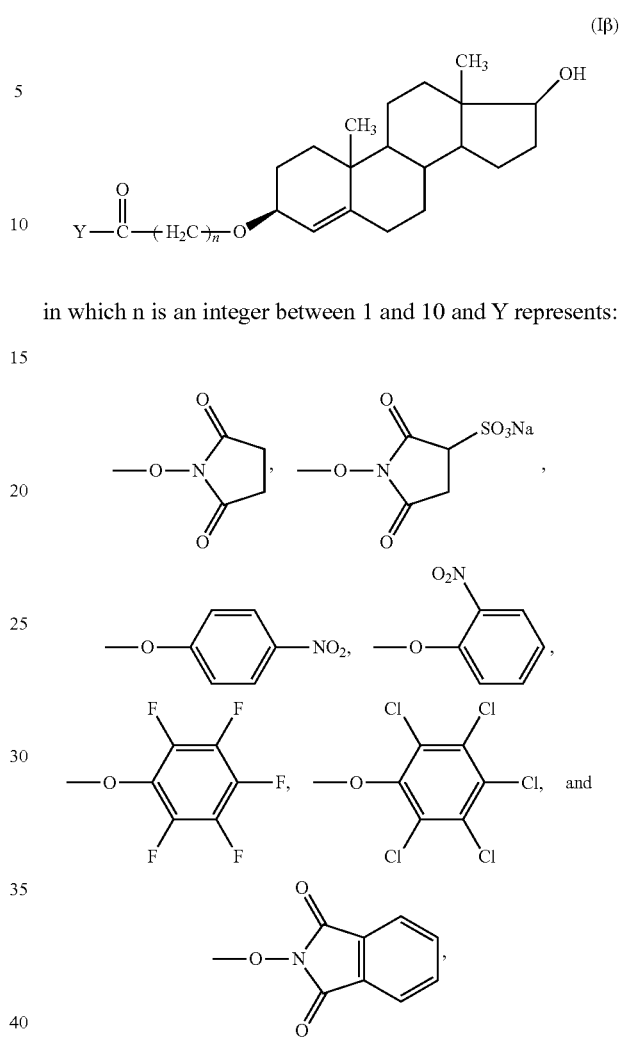

in which n is an integer between 1 and 10 and Y represents:

comprising or consisting of the steps consisting of:

(1) reacting testosterone with acetic anhydride to protect the OH function of position 17, and then with a reducing agent, in the presence of a solvent, to reduce the carbonyl in position 3 and obtain the compound of formula (IIβ):

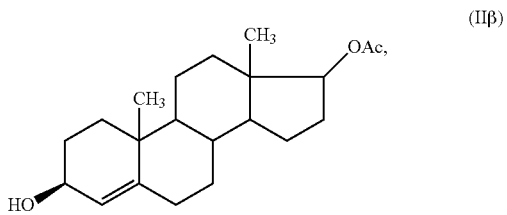

in which Ac means —CO—CH$_3$, (2) reacting the compound of formula (IIβ) thus obtained with the compound of formula (III): N$_2$CH—(CH$_2$)$_{n-1}$—COOC$_2$H$_5$, and then reacting with a base, in the presence of a solvent, to obtain the compound of formula (Iaβ):

(Iaβ)

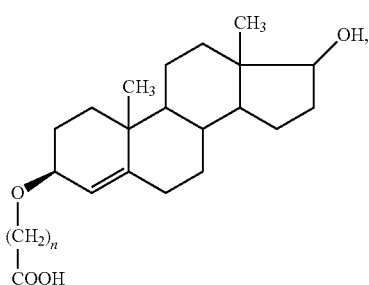

(3) reacting the compound of formula (Iaβ) thus obtained, in the presence of a carbodiimide derivative, with a reagent selected, depending on the final group Y, from the following compounds, to obtain the compounds of formula (Iβ):

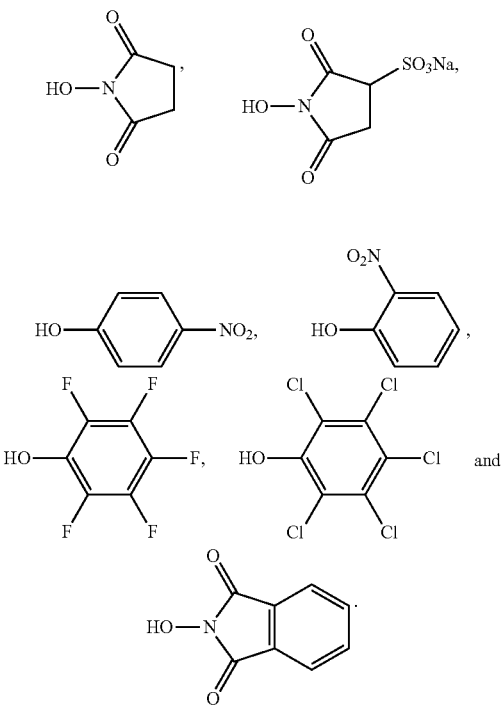

Yet another object of the invention relates to a method for preparing a testosterone derivative, in the form of a isomer in position 3, of the following general formula (Iα):

(Iα)

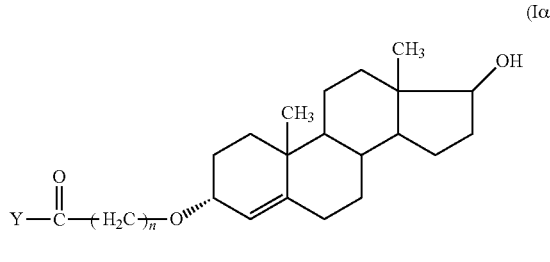

in which n is an integer between 1 and 10 and Y represents:

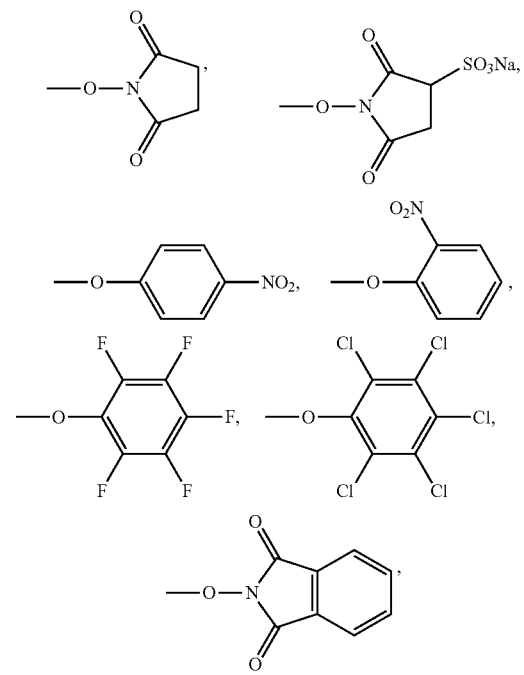

comprising or consisting of the steps consisting of:

(1) reacting testosterone with t-butyldimethylchlorosilane to protect the OH function of position 17, and then with a reducing agent, in the presence of a solvent, to reduce the carbonyl in position 3 and obtain the compound of formula (VIIIβ):

(VIIIβ)

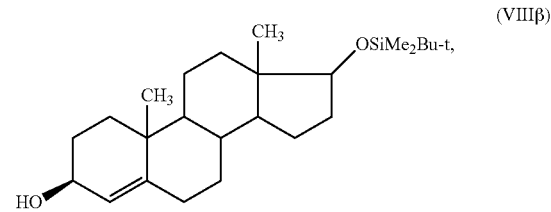

in which —SiMe₂Bu-t means t-butyldimethylsilanyl, (2) reacting the compound of formula (VIIIβ) thus obtained with triphenylphosphine, benzoic acid and diethyl azodicarboxylate, and then with a base, in the presence of a solvent, to transform, in position 3, the β isomer to a isomer and thus obtain the compound of formula (VIIIα):

(VIIIα)

in which —SiMe₂Bu-t means t-butyldimethylsilanyl, (3) reacting the compound of formula (VIIIα) thus obtained with the compound of formula (III): N₂CH—(CH₂)ₙ₋₁—COOC₂H₅, and then reacting with a base, in the presence of a solvent, to obtain the compound of formula (Iaα):

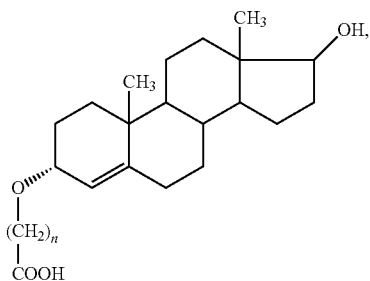
(Iaα)

(4) reacting the compound of formula (Iaα) thus obtained, in the presence of a carbodiimide derivative, with a reagent selected, depending on the final group Y, from the following compounds, to obtain a compound of formula (Iα):

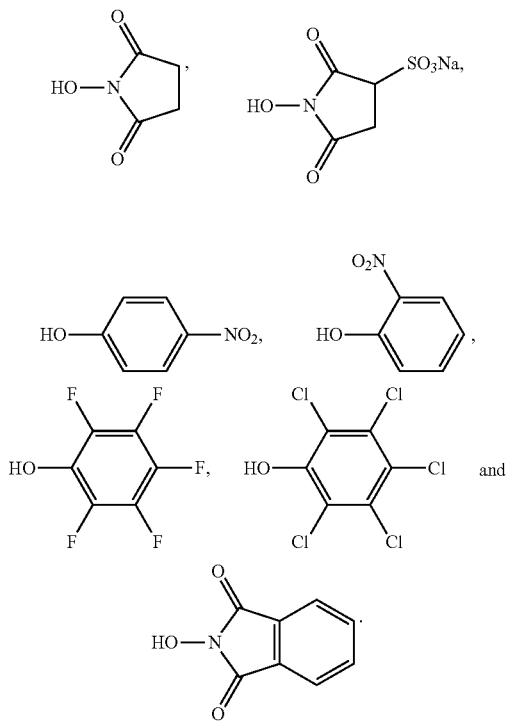

When Y represents:

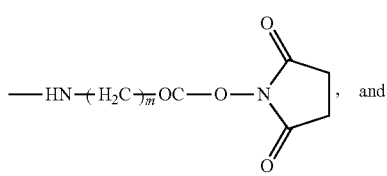, and

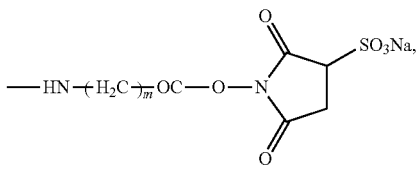

m being an integer as defined above, the testosterone derivatives then being compounds of formula (Iβ) or (Iα) depending on whether they are respectively β or α isomers in position 3, the methods of preparation comprise the preceding steps (1) and (2) for the β isomers and (1) to (3) for the α isomers, as well as steps (3) to (5) for the β isomers and (4) to (6) for the α isomers for preparing the compounds of formula (Ibβ) or (Ibα), as well as the following step:

1. reacting the compound of formula (Ibβ) or (Ibα) thus obtained, in the presence of a carbodiimide derivative, with a reagent selected, depending on the final group Y, from the following compounds, to obtain a compound of formula (Iβ) or (Iα):

Once again, activation of the ready-to-be-activated group of compound (Ib), Y=—COOH, is carried out using, in the presence of a carbodiimide derivative, one of the above two compounds which, when they lose the hydrogen of the hydroxyl group, become activated groups Y.

Thus, another object of the invention consists of a method for preparing a testosterone derivative, in the form of β isomer in position 3, of the following general formula (Iβ):

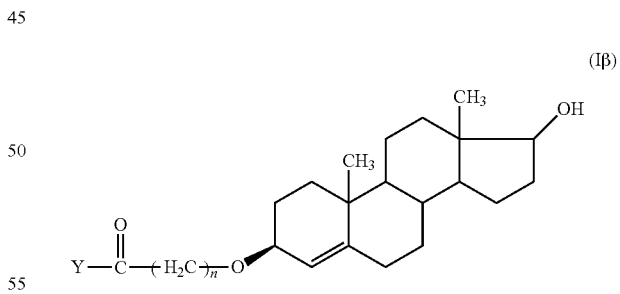
(Iβ)

in which n is an integer between 1 and 10 and Y represents:

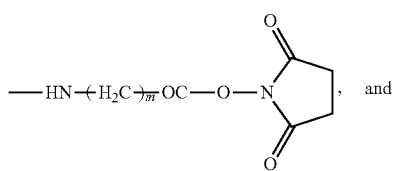, and

-continued

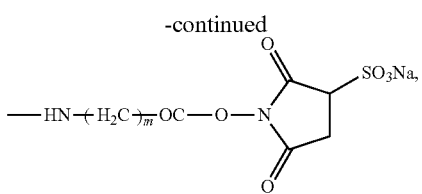

m being an integer between 1 and 10, the method comprising or consisting of the steps consisting of:
(1) reacting testosterone with acetic anhydride to protect the OH function of position 17, and then with a reducing agent, in the presence of a solvent, to reduce the carbonyl in position 3 and obtain the compound of formula (IIβ):

(IIβ)

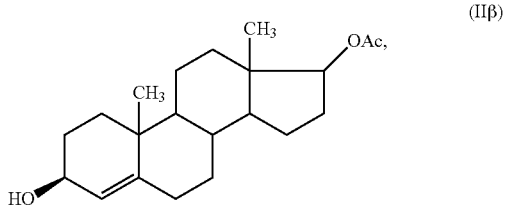

in which Ac means —CO—CH$_3$,
(2) reacting the compound of formula (IIβ) thus obtained with the compound of formula (III): N$_2$CH—(CH$_2$)$_{n-1}$—COOC$_2$H$_5$, and then reacting with a base, in the presence of a solvent, to obtain the compound of formula (Iaβ):

(Iaβ)

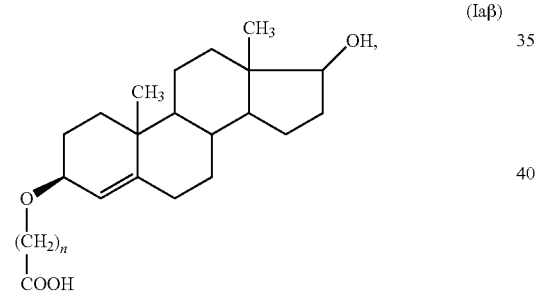

(3) reacting the compound of formula (Iaβ) thus obtained with N-hydroxysuccinimide, in the presence of a carbodiimide derivative, to produce the compound of formula (IVβ):

(IVβ)

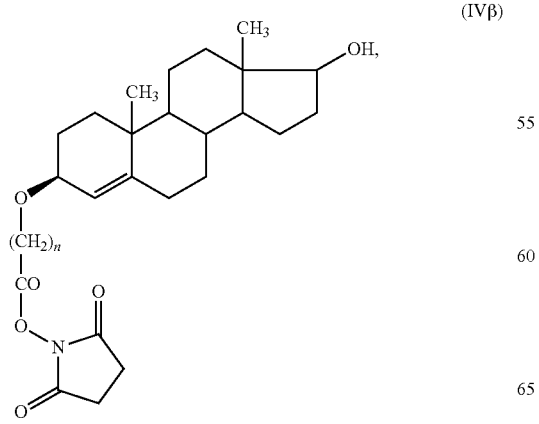

(4) reacting the compound of formula (Ivβ) thus obtained with the compound of formula (V): H$_2$N—(CH$_2$)m-COOR$_1$, in which R$_1$ is an alkyl or aryl group, to produce the compound of formula (VIβ):

(VIβ)

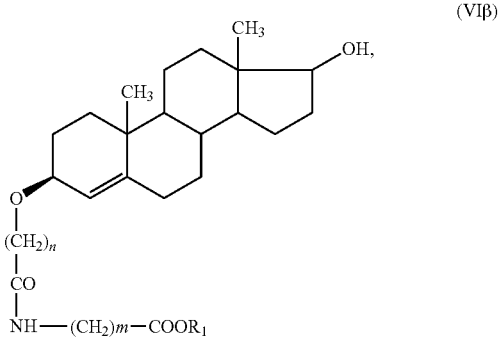

(5) reacting the compound of formula (VIβ) thus obtained with a base, in the presence of a solvent, to obtain the compound of formula (Ibβ):

(Ibβ)

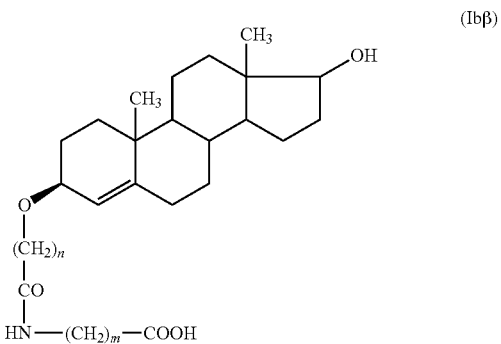

(6) reacting the compound of formula (Ibβ) thus obtained, in the presence of a carbodiimide derivative, with a reagent selected, depending on the final group Y, from the following compounds, to obtain the compounds of formula (Iβ):

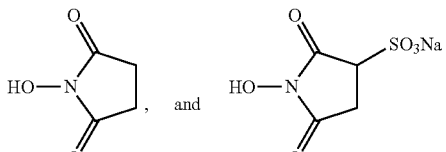

Yet another object of the invention consists of a method for preparing a testosterone derivative, in the form of α isomer in position 3, of the following general formula (Iα):

(Iα)

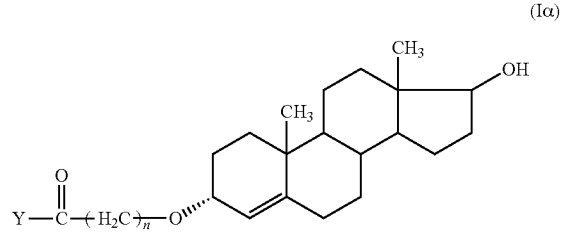

(Iα)

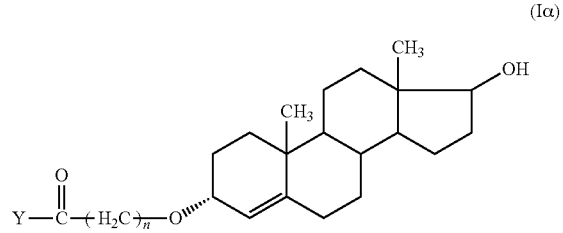

in which n is an integer between 1 and 10 and Y represents:

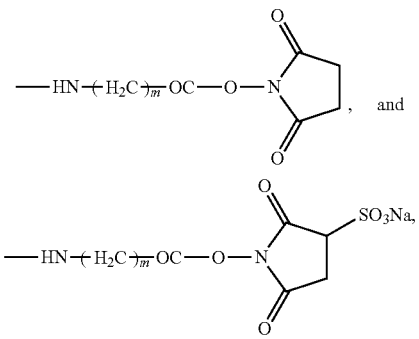

, and

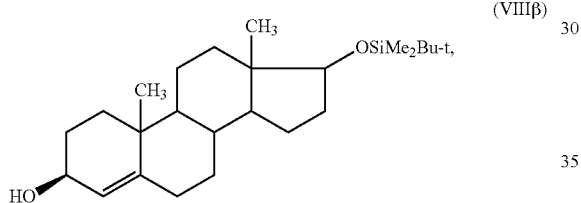

m being an integer between 1 and 10, the method comprising or consisting of the steps consisting of:

(1) reacting testosterone with t-butyldimethylchlorosilane to protect the OH function of position 17, and then with a reducing agent, in the presence of a solvent, to reduce the carbonyl in position 3 and obtain the compound of formula (VIIIβ):

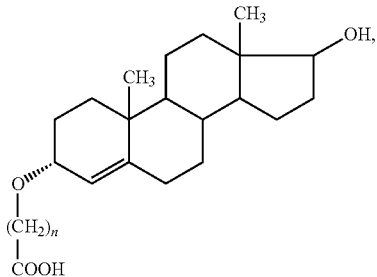

in which —SiMe$_2$Bu-t means t-butyldimethylsilanyl, (2) reacting the compound of formula (VIIIβ) thus obtained with triphenylphosphine, benzoic acid and diethyl azodicarboxylate, and then with a base, in the presence of a solvent, to transform, in position 3, the β isomer to a isomer and thus obtain the compound of formula (VIIIα):

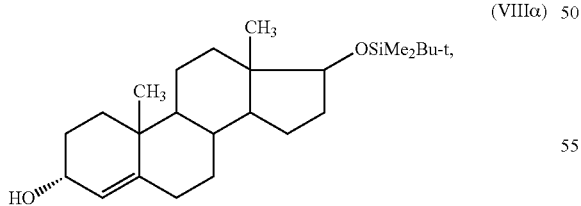

in which —SiMe$_2$Bu-t means t-butyldimethylsilanyl, (3) reacting the compound of formula (VIIIα) thus obtained with the compound of formula (III): N$_2$CH—(CH$_2$)$_{n-1}$—COOC$_2$H$_5$, and then reacting with a base, in the presence of a solvent, to obtain the compound of formula (Iaα):

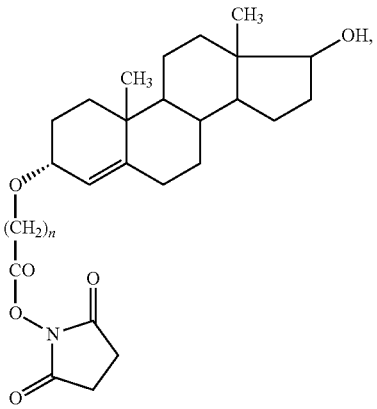

(4) reacting the compound of formula (Iaα) thus obtained with N-hydroxysuccinimide, in the presence of a carbodiimide derivative, to produce the compound of formula (IVα):

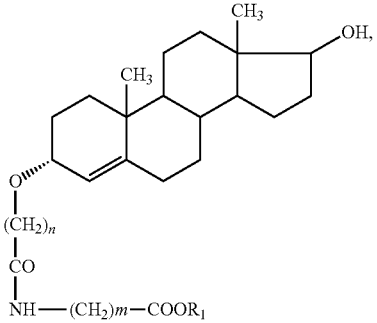

(5) reacting the compound of formula (IVα) thus obtained with the compound of formula (V): H$_2$N—(CH$_2$)m-COOR$_1$, in which R$_1$ is an alkyl or aryl group, to produce the compound of formula (VIα):

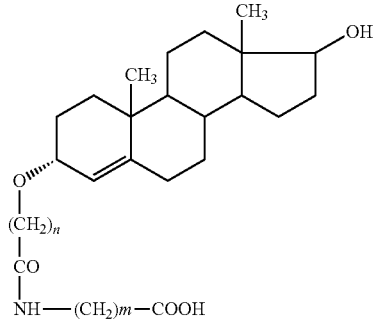

(6) reacting the compound of formula (VIα) thus obtained with a base, in the presence of a solvent, to obtain the compound of formula (Ibα):

(7) reacting the compound of formula (Ibα) thus obtained, in the presence of a carbodiimide derivative, with a reagent selected, depending on the final group Y, from the following compounds, to obtain a compound of formula (Iα):

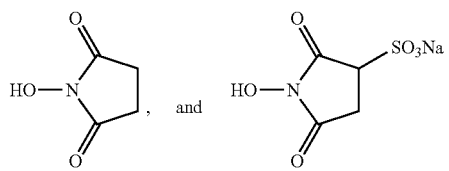

Finally, when Y represents $N_3$, the testosterone derivatives then being compounds of the following formula (Icβ) or (Icα) depending on whether they are respectively β or α isomers in position 3:

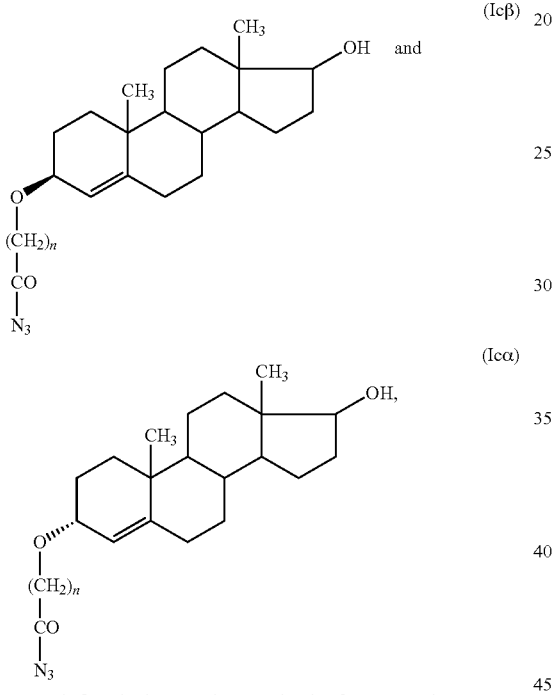

n being as defined above, the method of preparation comprises the preceding steps (1) and (2) for the β isomers and (1) to (3) for the α isomers, as well as the following two steps:

(1) reacting the compound of formula (Iaβ) or (Iaα) thus obtained, in the presence of a carbodiimide derivative, with $H_2NNH_2$, to obtain the compound of formula (VII):

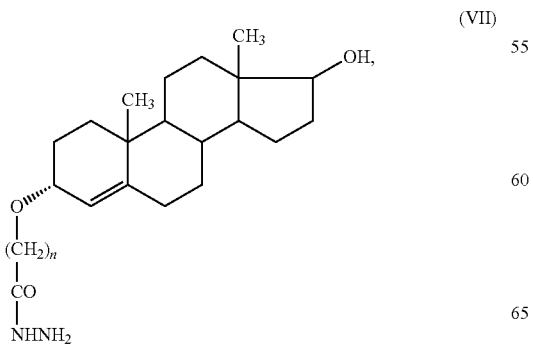

(2) reacting the compound of formula (VII) thus obtained with HONO to obtain the compound of formula (Icβ) or (Icα).

The derivative of carbodiimide used in this method is as defined above.

Thus, another object of the invention consists of a method for preparing a testosterone derivative, in the form of β isomer in position 3, of the following general formula (Icβ):

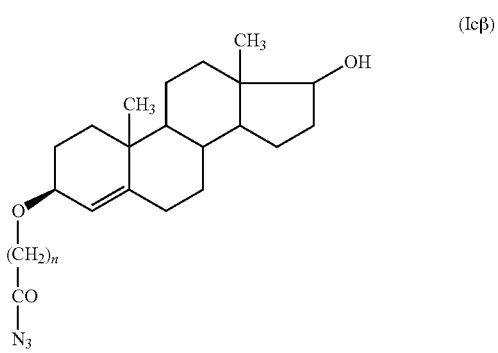

in which n is an integer between 1 and 10, the method comprising or consisting of the steps consisting of:

(1) reacting testosterone with acetic anhydride to protect the OH function of position 17, and then with a reducing agent, in the presence of a solvent, to reduce the carbonyl in position 3 and obtain the compound of formula (IIβ):

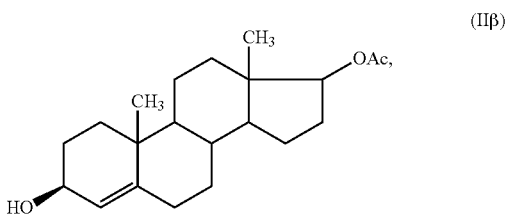

in which Ac means $—CO—CH_3$, (2) reacting the compound of formula (IIβ) thus obtained with the compound of formula (III): $N_2CH—(CH_2)_{n-1}—COOC_2H_5$, and then reacting with a base, in the presence of a solvent, to obtain the compound of formula (Iaβ):

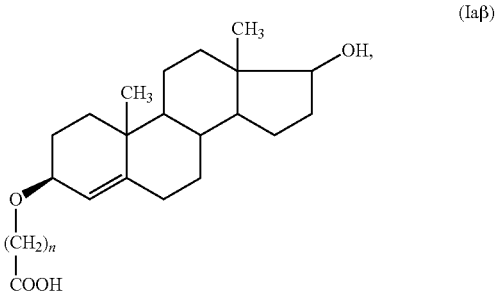

(3) reacting the compound of formula (Iaβ) thus obtained, in the presence of a carbodiimide derivative, with H$_2$NNH$_2$, to obtain the compound of formula (VIIβ):

(VIIβ)

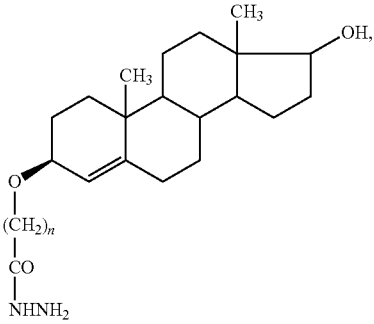

(3) reacting the compound of formula (VIIβ) thus obtained with HONO to obtain the compound of formula (Icβ).

The invention finally relates to a method for preparing a testosterone derivative, in the form of α isomer in position 3, of the following general formula (Icα):

(Icα)

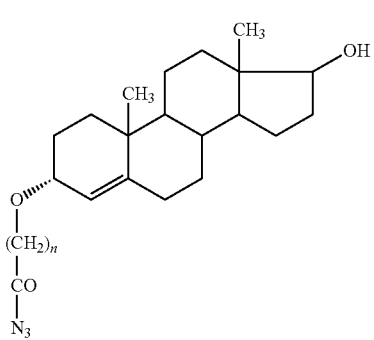

in which n is an integer between 1 and 10, the method comprising or consisting of the steps consisting of:
(1) reacting testosterone with t-butyldimethylchlorosilane to protect the OH function of position 17, and then with a reducing agent, in the presence of a solvent, to reduce the carbonyl in position 3 and obtain the compound of formula (VIIIβ):

(VIIIβ)

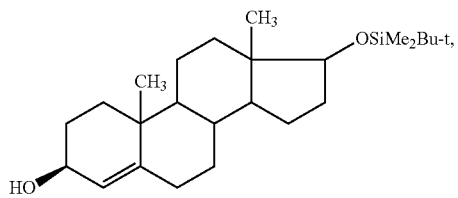

in which —SiMe$_2$Bu-t means t-butyldimethylsilanyl,
(2) reacting the compound of formula (VIIIβ) thus obtained with triphenylphosphine, benzoic acid and diethyl azodicarboxylate, and then with a base, in the presence of a solvent, to transform, in position 3, the β isomer to α isomer and thus obtain the compound of formula (VIIIα):

(VIIIα)

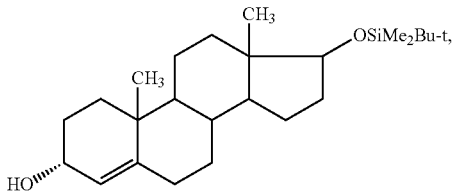

in which —SiMe$_2$Bu-t means t-butyldimethylsilanyl,
(3) reacting the compound of formula (VIIIα) thus obtained with the compound of formula (III): N$_2$CH—(CH$_2$)$_{n-1}$—COOC$_2$H$_5$, and then reacting with a base, in the presence of a solvent, to obtain the compound of formula (Iaα):

(Iaα)

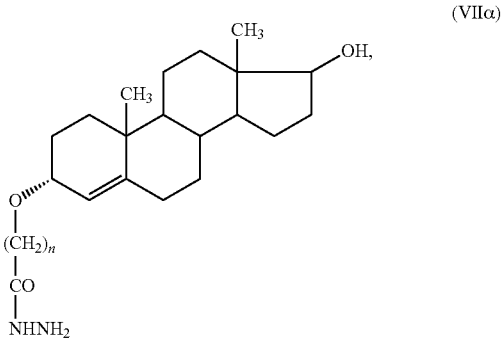

(4) reacting the compound of formula (Iaα) thus obtained, in the presence of a carbodiimide derivative, with H$_2$NNH$_2$, to obtain the compound of formula (VIIα):

(VIIα)

(4) reacting the compound of formula (VIIα) thus obtained with HONO to obtain the compound of formula (Icα).

The conjugates of the invention are prepared by any technique known by a person skilled in the art allowing formation of an amide bond between the compounds of formula (I) and a primary amine in another molecule, as described notably in Wong S. S., 1991.

Figure 2:
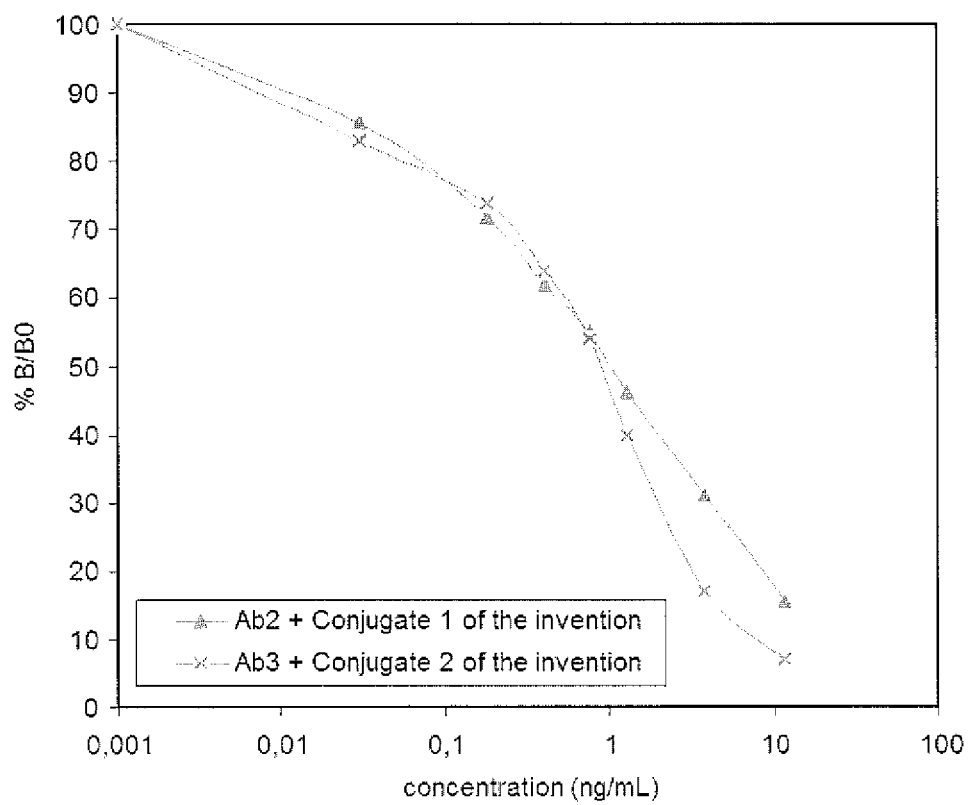

The invention will be better understood from the following examples, which are given for purposes of illustration and are nonlimiting, as well as from the figures, in which:

FIG. 1 shows a graph giving the ratio B/B0 as a percentage as a function of the concentration of the points of the standard range (logarithmic scale), for a reference assay (REF) using a conjugate of the prior art, a 2nd assay using a conjugate of the prior art (Ab1+VIDAS® conjugate) and two assays using a testosterone derivative of the invention (Ab2+Conjugate 1 of the invention, and Ab3+Conjugate 1 of the invention), FIG. 2 shows a graph giving the ratio B/B0 as a percentage as a function of the concentration of the points of the standard range (logarithmic scale), for an assay using Ab2+Conjugate 1 of the invention and an assay using Ab3+Conjugate 2 of the invention.

EXAMPLES

Analysis and control of the reaction in thin-layer chromatography (TLC) are carried out on a Merck silica gel plate (type 60, F254, thickness 0.2 mm), visualized using a UV lamp at 254 nm and developed with heat after spraying phosphomolybdic acid at 5% in ethanol (95%). The products are purified by 'flash chromatography' on Merck silica gel, 40-63 μm, pH 6.5 to 7.5.

The NMR spectra are recorded on the Broker Avance 250 apparatus. The chemical shifts δ are expressed in ppm on the basis of references: deuterated chloroform $CDCl_3$, δ=7.26 ppm for $^1H$ and 77.14 ppm for $^{13}C$; deuterated methanol $CD_3OD$, δ=4.90 ppm for $^1H$ and 49.0 for $^{13}C$; tetramethylsilane (TMS): δ=0 ppm for $^1H$ and $^{13}C$. The IR spectra are recorded on the Thermo-Nicolet FT-IR Avatar 360 apparatus and the Golden Gate option is used. The LC-MS analyses are carried out with the PE-Sciex API 100 LC-MS system, column $C_4$.

Example 1

Preparation of a Testosterone Derivative of the Invention of Formula (Iαβ)

17β-hydroxy-3β-carboxymethoxyandrost-4-ene or compound of formula (Iβ) in which n=1 and Y=—OH

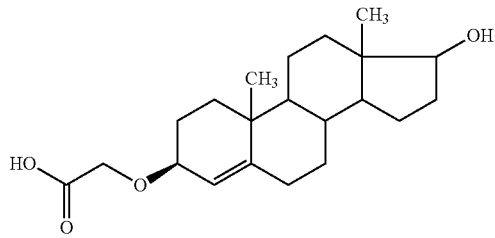 [SMILES: CC12CC[C@H](OCC(=O)O)C=C1CCC1C2CCC2(C)C(O)CCC12]

1.1 Preparation of
3β-hydroxy-17β-acetoxy-4-androstene (IIβ)

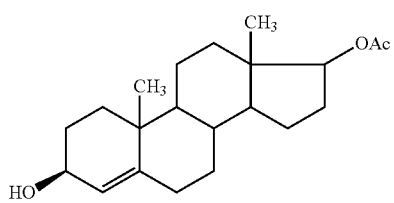 [SMILES: CC(=O)OC1CCC2C3CCC4=C[C@@H](O)CCC4(C)C3CCC12C]

A solution of 4.23 g (14.7 mmol) of testosterone in 8 ml of pyridine that has been dried over potassium hydroxide (KOH) overnight (5 g of KOH to 250 ml of pyridine) is prepared in a 250-ml flask equipped with magnetic stirring. The solution is cooled to 0° C. with a water/ice mixture. 4 ml of acetic anhydride is added to it dropwise. The reaction mixture is left to return to room temperature. The solution is stirred overnight at room temperature. The starting product is no longer found in analytical TLC (eluent: ethyl acetate/petroleum ether, 3/1, v/v). 30 ml of distilled water and 30 ml of ethyl acetate are poured into the flask and the mixture is stirred. The phases are separated with a separating funnel and the aqueous phase is extracted with 3×20 ml of ethyl acetate. The organic phases are combined and the solution obtained is washed with 20 nil of distilled water, dried over anhydrous magnesium sulfate ($MgSO_4$) and evaporated in a rotary evaporator. The product thus obtained is dried under reduced pressure using a vacuum pump for 4 hours to remove all the solvents. 4.8 g (yield=99.0%) of the intermediate 17β-acetoxy-4-androstene is obtained.

$^1H$ NMR ($CDCl_3$): δ 5.70 (1H, $H_4$), 4.60 (1H, $H_{17}$), 2.07 (3H, s), 1.16 (3H, s), 0.80 (3H, s). $^{13}C$ NMR ($CDCl_3$): δ 199.5, 171.0 (2C), 123.9, 82.5, 53.7, 50.2, 42.4, 38.6, 36.6, 35.7, 35.4, 33.9, 32.8, 31.5, 27.5, 23.5, 21.2, 20.5, 17.4, 12.1.

In a 250-ml flask equipped with magnetic stirring, 4.7 g (14.2 mmol) of 17β-acetoxy-4-androstene is dissolved in 20 ml of methanol and 3 ml of tetrahydrofuran (THF). The solution is then cooled to 0° C. with a water/ice mixture. 0.8 g (21.1 mmol) of sodium borohydride ($NaBH_4$) is added to the solution. The reaction is monitored on a TLC plate (eluent: ethyl acetate/petroleum ether, 1/1, v/v), checking for disappearance of the starting product. Once all of the starting product has been consumed, 10 ml of acetone is added to stop the reaction. The solution is left to return to room temperature and the solution is evaporated in the evaporator at 30° C. 30 ml of distilled water and 30 ml of ethyl acetate are poured into the flask. The mixture is stirred and the phases are decanted. The aqueous phase is extracted with 3×30 ml of ethyl acetate. The organic phases are combined, washed with 30 ml of distilled water, dried over anhydrous $MgSO_4$ and finally evaporated to dryness under reduced pressure at 30° C. 4.6 g (yield=97.3%) of the product (IIβ) is obtained after purification by silica gel chromatography (eluent: ethyl acetate/petroleum ether, 111, v/v).

$^1H$ NMR ($CDCl_3$): δ 5.30 (1H, $H_4$), 4.61 (1H, t, $H_{17}$), 4.18 (1H, $H_3$), 2.04 (3H, s), 1.05 (3H, s), 0.80 (3H, s). $^{13}C$ NMR ($CDCl_3$): δ 171.3, 147.3, 123.7, 82.8, 67.9, 54.4, 50.5, 42.6, 37.4, 36.8, 35.8, 35.5, 32.6, 32.1, 29.5, 27.5, 23.6, 21.3, 20.6, 19.0, 12.1.

1.2 Preparation of the Testosterone Derivative of the Invention of Formula (Iαβ)

The dry reaction solvent dichloromethane ($CH_2Cl_2$) is prepared by distillation of 250 ml of $CH_2Cl_2$ on 5 g of phosphorus pentoxide ($P_2O_5$).

A 250-ml three-necked flask equipped with magnetic stirring, a dropping funnel and an inert gas supply is purged with dry nitrogen for 10 min. 2.2 g (6.6 mmol) of 3β-hydroxy-17β-acetoxy-4-androstene (IIβ), 10 ml of dry dichloromethane and 20 mg (0.045 mmol) of rhodium(II) acetate dimer $[Rh(OAc)_2]_2$ are introduced under nitrogen. The mixture obtained is cooled to 0° C. A solution of 2.5 ml (2.71 g, 23.8 mmol) of ethyl diazoacetate ($N_2CHCOOEt$) in 5 ml of dry dichloromethane is prepared and introduced into the dropping funnel. The solution is added to the three-necked flask under nitrogen, with stirring, over the course of 70 min. The reaction mixture is left to return to room temperature and stirring is maintained for 4 hours. The presence of a small amount of the starting product can still be found in TLC (eluent: ethyl acetate/petroleum ether, 1/1, v/v). So that the reaction goes to completion, 2.5 mg (0.006 mmol) of [Rh(OAc)$_2$]$_2$ is added. A solution of 0.5 ml (4.8 mmol) of N$_2$CHCOOEt in 2 nil of dry dichloromethane is introduced into the three-necked flask via the dropping funnel over the course of 10 min at room temperature. 20 ml of distilled water and 20 ml of dichloromethane are poured in and the mixture is stirred for 10 min. The phases are separated and the aqueous phase is extracted with 2×20 nil of dichloromethane. The organic phases are collected, dried over anhydrous MgSO$_4$ and evaporated to dryness using a rotary evaporator at 25° C. to give the crude product in the form of yellow oil. Purification is carried out by silica gel chromatography (eluent: ethyl acetate/petroleum ether, 1/3, v/v). 2.4 g (yield=86.6%) of the product 3β-carboxymethoxy-17β-acetoxy-4-androstene ethyl ester is obtained.

$^1$H NMR (CDCl$_3$): δ 55.39 (1H), 4.54 (1H, t), 4.23 (2H, q), 4.13 (1H), 2.03 (s), 1.29 (t), 1.05 (s), 0.80 (s). $^{13}$C NMR (CDCl$_3$): δ 171.2, 170.9, 148.1, 120.4, 82.7, 76.0, 65.5, 61.2, 54.3, 50.4, 42.5, 37.5, 36.8, 35.6, 35.2, 32.5, 32.1, 27.5, 25.2, 23.5, 21.2, 20.4, 18.8, 14.0, 12.0. MS (LC-MS): 347.0 (M−H)$^-$.

2.0 g (4.8 mmol) of 3β-carboxymethoxy-17β-acetoxy-4-androstene ethyl ester and 20 ml of methanol are put in a 250-ml flask equipped with magnetic stirring. The mixture is cooled to 0° C. 10 ml (1.0M, 10 mmol) of sodium hydroxide solution (NaOH) is added. Stirring is maintained at 0° C. for 3 hours. The reaction mixture is left to return to room temperature and the saponification reaction is completed after 20 hours of stirring. The reaction mixture is neutralized with hydrochloric acid (HCl, 1.0N) at pH 6 and then evaporated at 25° C. with a rotary evaporator. The residue is purified on a silica column gel to give 1.3 g (yield=78.0%) of the product (Iaβ).

$^1$H NMR (CD$_3$OD): δ 5.32 (1H, H$_4$), 3.83 (2H), 3.50 (1H, t), from 2.40 to 1.10 (m), 1.01 (3H, s), 0.69 (3H, s). $^{13}$C NMR (CD$_3$OD): δ 174.5, 148.9, 119.8, 81.9, 76.3, 64.8, 54.5, 50.7, 42.9, 37.6, 36.6, 35.9, 35.2, 32.6, 32.2, 30.3, 25.2, 23.4, 20.6, 18.9, 11.1. IR (cm$^{-1}$): 3383, 2928, 2869, 2847, 1721, 1529, 1432, 1377, 1336, 1243, 1213, 1110, 1050.

Example 2

Preparation of a Testosterone Derivative of the Invention of Formula (Iβ)

17β-hydroxy-3β-carboxymethoxy-androst-4-ene N-hydroxysuccinimide ester or compound of formula (I) in which n=1 and Y=

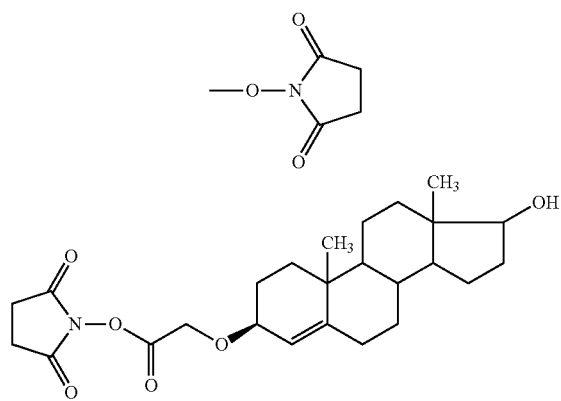

The procedure described in example 1 was repeated, then continuing as follows.

10 ml of 1,2-dimethoxyethane (DME) distilled on calcium hydride (CaH$_2$), 100 mg (0.287 mmol) of the compound of formula (Iaβ) prepared in example 1, and 33 mg (0.287 mmol) of N-hydroxysuccinimide (HOSu) are put in a 25-ml flask equipped with magnetic stirring. The mixture is cooled to 0° C. 59 mg (0.287 mmol) of 1,3-dicyclohexylcarbodiimide (DCC) is added. Stirring is maintained at temperature for 15 hours. TLC (eluent: chloroform/acetone/acetic acid, 70/25/1, v/v/v) shows almost complete disappearance of the starting product. The reaction mixture is filtered and the filtrate is evaporated at room temperature under reduced pressure. 6.0 ml of anhydrous dichloromethane is added to the residue and the mixture thus obtained is then filtered. The solution is evaporated to dryness at room temperature with a rotary evaporator. The product is dried under vacuum for 4 hours. 64 mg (50.0%) of the product (IVβ, n=1) is obtained.

$^1$H NMR (CDCl$_3$): δ 5.38 (1H, H$_4$), 4.47 (2H), 4.40 (1H, t, H$_{17}$), from 4.20 to 3.40 (4H, m), 2.85 (4H, s), from 2.60 to 1.10 (m), 1.05 (3H, s), 0.74 (3H, s). $^{13}$C NMR (CDCl$_3$): δ 168.9, 166.6, 149.2, 119.7, 81.9, 76.9, 63.2, 54.5, 50.7, 42.9, 37.6, 36.6, 36.0, 35.1, 32.6, 32.2, 30.5, 25.7, 25.2, 23.4, 20.6, 18.9, 11.2. IR (cm$^{-1}$): 3537, 3323, 2929, 2849, 1784, 1732, 1203, 1071. IR (cm$^{-1}$): 3536, 3507, 3322, 2928, 2849, 1783, 1731, 1624, 1573, 1442, 1426, 1376, 1203, 1071. MS (LC-MS): 446 (M+H)$^+$, 908 (2M+H$_2$O)$^+$.

Example 3

Preparation of a Testosterone Derivative of the Invention of Formula (Ibβ)

Compound of formula (Iβ) in which n=1 and Y=—NH—CH$_2$—COOH

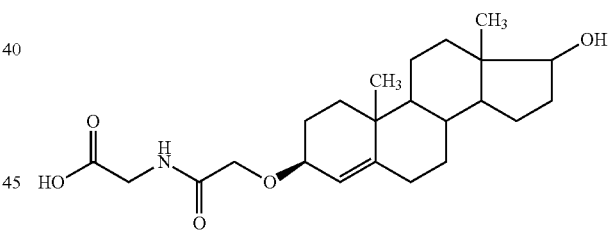

The procedure described in example 1 was repeated, then continuing as follows.

3.1 Preparation of the Compound of Formula (VIβ) in which m=n=1

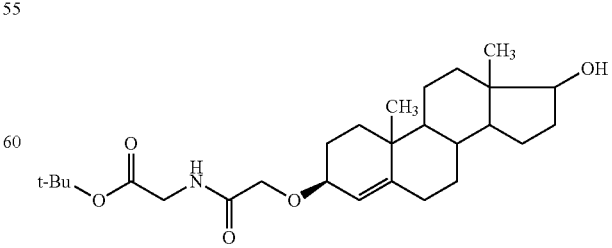

The product from example 1 (Iaβ) (500 mg, 1.43 mmol) and 30 ml of anhydrous DME are put in a 100-ml flask.

N-Hydroxysuccinimide (HOSu, 247.7 mg, 2.15 mmol) is added. The mixture is stirred and 1,3-dicyclohexylcarbodiimide (DCC, 440 mg, 2.15 mmol) is then added. Stirring is maintained at room temperature overnight. The reaction mixture is filtered, and the filtrate containing the compound (IVβ, n=1) is used directly for the rest of the synthesis.

Sodium bicarbonate solution (NaHCO$_3$, 1.0N, 10 ml) and 1.0 ml of product tert-butyl glycine ester (H$_2$NCH$_2$COOBu$^t$) are added to the filtrate. The mixture formed is stirred at room temperature for 12 hours. 70 ml of distilled water and 50 ml of ethyl acetate are mixed with the reaction mixture. The phases are decanted and the phase is extracted with ethyl acetate (3×50 ml). The combined organic solution is dried over anhydrous MgSO$_4$ and then evaporated using a rotary evaporator at 30° C. The residue is purified by chromatography (eluent: ethyl acetate 100%). 401 mg (yield=60.2%) of the product (VIβ, m=n=1) is formed in the form of white crystals.

$^1$H NMR (CDCl$_3$): δ 7.19 (1H), 5.32 (1H), 4.35 (1H), 4.01 (2H, s), 3.94 (2H, d), 3.64 (1H, t), from 2.30 to 0.80 (m), 1.45 (s), 1.04 (s), 0.73 (s). $^{13}$C NMR (CDCl$_3$): δ 170.6, 168.8, 148.8, 120.0, 82.3, 81.8, 76.3, 67.0, 54.5, 50.7, 42.9, 41.4, 37.6, 36.6, 36.0, 35.1, 32.6, 32.2, 30.5, 28.1, 25.5, 23.4, 20.6, 18.9, 11.1.

3.2 Preparation of the Testosterone Derivative of Formula (Ibβ) in which m=n=1

400 mg (0.87 mmol) of the tert-butyl ester (VIβ, n=1) prepared is dissolved in 30 ml of methanol. 2.0 ml of sodium hydroxide solution (NaOH, 1.0N) is added. Stirring is maintained at room temperature for 15 hours. The reaction mixture is neutralized with hydrochloric acid (HCl, 1.0N) at pH=6. The solution thus formed is evaporated at 30° C. under reduced pressure. The crude product obtained is purified by chromatography with a methanol/chloroform eluent (20/80, v/v). 340 mg (yield=96.8%) of the derivative of formula (Ibβ, m=n=1) is obtained in the form of white crystals.

$^1$H NMR (CD$_3$OD): δ 5.35 (1H), 3.96 (2H, s), 3.86 (2H, s), 3.50 (1H, t), 3.25 (1H), from 2.30 to 0.70 (m), 1.02 (3H, s), 0.69 (3H, s). $^{13}$C NMR (CD$_3$OD): δ 173.5, 173.4, 149.5, 121.5, 82.3, 77.5, 67.7, 56.1, 52.0, 44.0, 42.0, 38.6, 37.9, 37.3, 36.4, 34.7, 33.9, 33.2, 30.5, 24.3, 21.7, 19.3, 11.6. IR (cm$^{-1}$): 3371, 3322, 2922, 2848, 1714, 1622, 1537, 1437, 1420, 1230, 1077. MS (LC-MS): 406.6 (M+H)$^+$, 405.4 (M−H)$^−$.

Example 4

Preparation of a Testosterone Derivative of the Invention of Formula (Iβ)

Compound Iβ of formula (I) in which m=n=1 and Y=

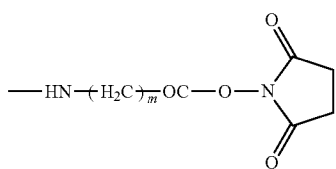

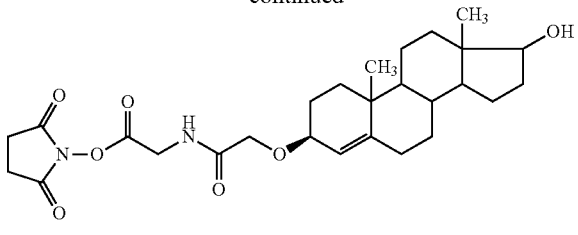

The procedure described in example 3 was repeated, then continuing as follows.

The product of formula (Ibβ) obtained in example 3 (220 mg, 0.54 mmol) is dissolved in 15 ml of anhydrous tetrahydrofuran (THF) in a flask equipped with magnetic stirring. 62.5 mg (0.54 mmol) of N-hydroxysuccinimide (HOSu) is introduced and a transparent solution is formed. 112 mg (0.54 mmol) of 1,3-dicyclohexylcarbodiimide (DCC) is added. The mixture is stirred at room temperature for 4 hours 30 min. The reaction mixture is filtered and the filtrate is evaporated without heating using a rotary evaporator. The residue obtained is washed with 6.0 ml of anhydrous dichloromethane, and then dried under vacuum. 190 mg (yield=70.1%) of the ester (Iβ) is produced. $^1$H NMR (CDCl$_3$): δ 7.20 (1H), 5.35 (1H), 4.45 (H, d), 4.05 (2H), 3.98 (1H), 3.64 (1H, t), 2.84 (4H, m), from 2.60 to 0.80 (m), 1.04 (3H, s), 0.73 (3H, s). $^{13}$C NMR (CDCl$_3$): δ 171.0, 168.7, 165.6, 149.1, 119.8, 81.8, 76.5, 66.8, 54.5, 50.7, 42.9, 38.3, 37.6, 36.6, 36.0, 35.0, 33.8, 32.6, 32.3, 30.4, 25.6, 23.4, 20.6, 18.9, 11.1. MS (Fab, Na): 501 (M−1)$^+$, 525 (M+Na)$^+$.

Example 5

Preparation of a Testosterone Derivative of the Invention of Formula (Iaα)

17β-hydroxy-3α-carboxymethoxy-androst-4-ene or compound of formula (Iα) in which n=1 and Y=—OH

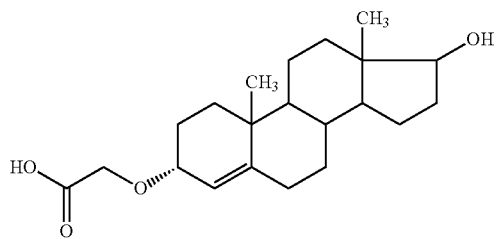 [SMILES: CC12CC[C@@H](OCC(=O)O)C=C1CCC1C2CCC2(C)C(O)CCC12]

5.1 Preparation of 3β-hydroxy-17β-O-(t-butyldimethylsilyl)-4-androstene (VIIIβ)

2.88 g (10 mmol) of testosterone, 12 ml of anhydrous N,N'-dimethylformamide (DMF) and 1.0 g (14.7 mmol) of imidazole are put in a 250-ml flask under nitrogen. 2.26 g (15 mmol) of tert-butyldimethylchlorosilane (ClTBDMS) is added. The mixture is stirred under nitrogen at room temperature for 4 hours 30 min. 100 ml of distilled water and 100 ml of ethyl acetate are poured into the reaction mixture and the mixture is stirred. The phases are separated and the aqueous phase is extracted with ethyl acetate (3×70 ml). The combined organic solution is washed with 100 ml of distilled water, dried on anhydrous MgSO$_4$ and evaporated. The residue is purified by silica gel chromatography (eluent:

ethyl acetate/petroleum ether, 1/5, v/v) to give 3.67 g of the reaction product in the form of white crystals.

3.66 g of this product obtained is mixed with 40 ml of methanol, 10 mg of hydrated cerium(III) chloride ($CeCl_3 \cdot 7H_2O$) in a 250-ml flask equipped with magnetic stirring. A suspension is formed. 0.40 g (10.6 mmol) of sodium borohydride ($NaBH_4$, 98%) is added in 3 portions over the course of 5 min. Stirring is maintained at temperature for 10 min. The reaction mixture is evaporated at 30° C. using a rotary evaporator under reduced pressure. The residue is mixed with 50 ml of ethyl acetate and 50 ml of distilled water. The phases are decanted and the aqueous phase is extracted with ethyl acetate (2×50 ml). The organic solution collected is dried over anhydrous $MgSO_4$ and evaporated to give the crude product, which is then purified by silica gel chromatography (eluent: ethyl acetate/petroleum ether, 1/4, v/v). 3.5 g (yield=86.5%) of the product (VIIIβ) is formed in the form of white crystals.

$^1$H NMR ($CDCl_3$): δ 5.29 (1H, $H_4$), 4.18 (1H, $H_3$), 3.56 (1H, t, $H_{17}$), from 2.40 to 0.80 (m), 1.08 (3H, s, $H_{19}$), 0.89 (9H, s, t-Bu), 0.74 (3H, s, $H_{18}$), 0.02 (6H, s, $Me_2Si$). $^{13}$C NMR ($CDCl_3$): δ 147.8, 123.5, 81.8, 68.0, 54.8, 50.5, 43.3, 37.2, 37.1, 36.1, 35.5, 32.8, 32.2, 31.0, 29.6, 25.9, 23.6, 20.8, 19.1, 18.9, 11.4, −4.3, −4.6.

5.2 Preparation of 3α-hydroxy-17β-O-(t-butyldimethylsilyl)-4-androstene (IXα)

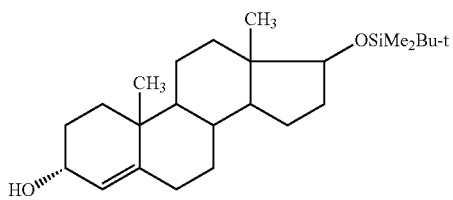

A 500-ml flask is charged under nitrogen with 4.46 g (11.0 mmol) of the product (VIIIβ) prepared, 50 ml of anhydrous benzene, 5.78 g (22.0 mmol) of triphenylphosphine and 2.69 g (22.0 mmol) of benzoic acid. 3.84 g (22.0 mmol) of diethyl azodicarboxylate (DEAD) is dissolved in 10 ml of anhydrous benzene and the solution obtained is added dropwise to the flask under nitrogen shielding for 10 min. The reaction mixture is stirred at room temperature for 1 hour. 50 ml of sodium bicarbonate solution ($NaHCO_3$, 1.0 M) is poured into the mixture and the phases are separated. The aqueous phase is extracted with ethyl acetate (3×30 ml) and the combined organic solution is washed with 50 ml of $NaHCO_3$ solution (1.0 M), then with 50 ml of distilled water, dried over anhydrous $MgSO_4$ and evaporated. The residue is taken up in 150 ml of ethanol, and 30 ml of sodium hydroxide solution (NaOH, 1.0 N) is added. The mixture is stirred at room temperature overnight and at 70° C. for 3 hours. There is no longer any starting product on TLC (eluent: ethyl acetate/petroleum ether, 1/9, v/v). The reaction mixture is evaporated to 50 ml with a rotary evaporator. 50 ml of distilled water and 100 ml of ethyl acetate are added. The phases are separated after stirring. The aqueous phase is extracted with ethyl acetate (2×70 ml). The organic solution obtained is washed with distilled water (70 ml), dried over anhydrous $MgSO_4$ and evaporated under reduced pressure to give the crude product. Purification is carried out by silica gel column chromatography (eluent: ethyl acetate/petroleum ether, 1/7, v/v). 2.19 g (yield=47.1%) of the product (IXα) is obtained.

$^1$H NMR ($CDCl_3$): δ 5.45 (1H, $H_4$), 4.07 (1H, $H_3$), 3.52 (1H, t, $H_{17}$), from 2.40 to 0.80 (m), 0.97 (3H, s, $H_{19}$), 0.86 (9H, s, t-Bu), 0.71 (3H, s, $H_{18}$), 0.00 (6H, s, $Me_2Si$). $^{13}$C NMR ($CDCl_3$): δ 150.2, 120.8, 81.7, 64.2, 54.3, 50.4, 43.3, 37.6, 37.1, 35.9, 32.4 (2C), 31.7, 30.9, 27.9, 25.9, 23.6, 21.2, 18.2, 18.1, 11.4, −4.3, −4.7.

5.3 Preparation of the Testosterone Derivative of Formula (Iaα)

In a 250-ml three-necked flask equipped with magnetic stirring, 3.95 g (9.8 mmol) of the product (IXα) is dissolved in 65 ml of anhydrous dichloromethane under nitrogen. 100 mg of rhodium(II) acetate dimer is added. The solution is cooled to 0° C. A solution of 4.0 g (35 mmol) of ethyl diazoacetate in 25 ml of anhydrous dichloromethane is prepared and added dropwise to the three-necked flask under nitrogen for 1 hour. The reaction mixture is left to return to room temperature and stirring is maintained for 4 hours. 100 ml of distilled water is added and the phases are separated. The aqueous phase is extracted with ethyl ether (3×100 ml). The combined organic solution is dried over anhydrous $MgSO_4$ and evaporated. The residue obtained is purified on a silica gel chromatographic column (eluent: ethyl acetate/petroleum ether, 1/6, v/v) to give 3.2 g of product, which is used directly for the rest of the synthesis.

3.0 g of the product thus obtained is dissolved in 20 ml of anhydrous tetrahydrofuran (THF) and the solution is cooled to 0° C. 15 ml of solution of tetra-n-butylammonium fluoride ($Bn_4NF$, 1.0 M in THF) is added under nitrogen. The reaction mixture is left to return to room temperature and stirring is maintained for 22 hours. The reaction mixture is evaporated using a rotary evaporator. 100 ml of distilled water and 100 ml of ethyl ether are mixed with the residue. The phases are decanted and the phase is extracted with ethyl ether (3×50 ml). The organic solution is dried over anhydrous $MgSO_4$ and evaporated. Purification of the residue formed by silica gel chromatography (eluent: ethyl acetate/petroleum ether, 1/1, v/v) gives 1.0 g of product (transparent oil), which is then dissolved in 30 nil of ethanol. 6.0 ml of sodium hydroxide solution (NaOH, 1.0 N) is added to the solution at room temperature and the mixture is stirred for 30 min. TLC (eluent: chloroform/acetone/acetic acid, 70/25/2, v/v/v) is used for monitoring the evaluation of saponification. The reaction mixture is neutralized with hydrochloric acid (HCl, 1.0 N) at pH 6 and is evaporated to dryness at room temperature under reduced pressure. The crude product thus formed is purified on a silica gel chromatographic column (eluent: chloroform/methanol, 4/1, v/v). 950 mg of the product (Iaα) is obtained.

$^1$H NMR ($CDCl_3$): δ 5.44 (1H, $H_4$), 4.11 (2H, s), 3.84 (1H, $H_3$), 3.63 (1H, t, $H_{17}$), from 2.40 to 0.80 (m), 1.01 (3H, s, $H_{19}$), 0.78 (3H, s, $H_{18}$). $^{13}$C NMR ($CD_3OD$): δ 175.8, 152.2, 119.2, 82.4, 73.5, 66.7, 55.3, 52.0, 44.0, 38.7, 37.9, 37.2, 33.6, 33.4, 33.1, 30.5, 25.0, 24.2, 22.2, 18.7, 11.6. IR ($cm^{-1}$): 3375, 2925, 2869, 2846, 1725, 1589, 1434, 1213, 1105, 1072. MS (LC-MS): 347.2 (M−H)$^-$.

Example 6

Preparation of a Testosterone Derivative of the Invention of Formula (Iα)

17β-hydroxy-3α-carboxymethoxy-androst-4-ene N-hydroxysuccinimide ester or compound of formula (Iα) in which n=1 and Y=

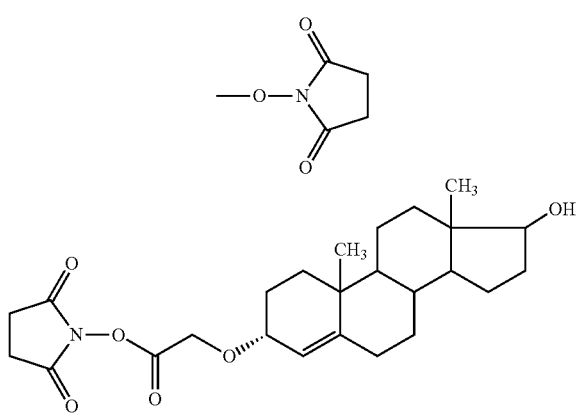

The procedure described in example 5 was repeated, then continuing as follows.

100 mg (0.29 mmol) of the product (Iaα) synthesized in example 5, 34.1 mg (0.29 mmol) of N-hydroxysuccinimide (HOSu) and 18 ml of anhydrous tetrahydrofuran (THF) are put in a 50-ml flask equipped with magnetic stirring. A suspension is obtained. 59.8 mg (0.29 mmol) of 1,3-dicyclohexylcarbodiimide (DCC) is added. The mixture is stirred at room temperature overnight. The reaction mixture is filtered and the filtrate is evaporated at 25° C. 5 ml of anhydrous dimethoxymethane is added and the mixture is filtered. The filtrate is evaporated at 25° C. using a rotary evaporator. The residue is dried using a vacuum pump, washed with 5 ml of anhydrous hexane and dried under reduced pressure. 86 mg (66.5%, purity: 90% in HPLC) of the testosterone derivative (Iα) is obtained.

$^1$H NMR (CDCl$_3$): δ 5.50 (1H, H$_4$), 4.44 (2H, s), 3.85 (1H, H$_3$), 3.61 (1H, t, H$_{17}$), 2.84 (4H, s), from 2.40 to 0.80 (m), 0.97 (3H, s, H$_{19}$), 0.74 (3H, s, H$_{18}$). $^{13}$C NMR (CDCl$_3$): δ 169.0, 166.7, 152.2, 117.2, 81.9, 73.3, 63.6, 53.9, 50.6, 43.0, 37.7, 36.6, 35.8, 32.4, 32.2, 31.9, 30.4, 25.6, 24.2, 23.4, 21.1, 18.1, 11.1. IR (cm$^{-1}$): 3517, 3324, 2917, 2848, 1780, 1729, 1703, 1427, 1379, 1204, 1066. MS (LC-MS): 447.2 (M+H)$^+$.

Example 7

Preparation of a Testosterone Derivative of Formula (Ibα)

Compound of formula (Iα) in which n=1 and Y=—NH—CH$_2$—COOH

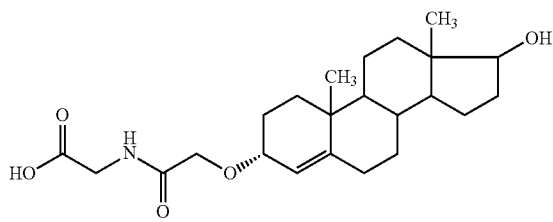 [SMILES: CC12CC[C@@H](OCC(=O)NCC(=O)O)C=C1CCC1C2CCC2(C)C(O)CCC12]

The procedure described in example 5 was repeated, then continuing as follows.

7.1 Preparation of the Compound (VIα) in which m=n=1

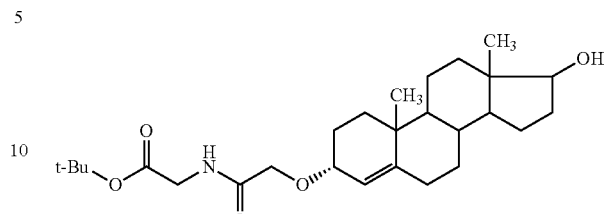

380 mg (1.09 mmol) of the product (Iaα), 125.5 mg (1.09 mmol) of N-hydroxysuccinimide (HOSu) and 30 ml of anhydrous tetrahydrofuran (THF) are mixed in a 100-ml flask under nitrogen shielding. 225 mg (1.09 mmol) of 1,3-dicyclohexylcarbodiirnide (DCC) is added. The mixture is stirred at room temperature for 4 hours. TLC (eluent: chloroform/methanol, 5/1, v/v) is used for monitoring the reaction. The mixture containing the product (IVα, n=1) is filtered.

6 ml of sodium bicarbonate solution (NaHCO$_3$, 1.0 M) and 142 mg (1.09 mmol) of glycine tert-butyl ester are quickly added to the filtrate. The mixture is stirred at 25° C. for 30 min, and then concentrated to 10 ml under reduced pressure. 50 ml of distilled water and 50 ml of ethyl acetate are added. The phases are decanted and the aqueous phase is extracted with ethyl acetate (3×50 ml). The organic solution is collected and dried over MgSO$_4$ and evaporated. The crude product is then purified on a silica gel chromatographic column (eluent: ethyl acetate 100%) to give 440 mg of the product (VIα, m=n=1).

$^1$H NMR (CDCl$_3$): δ 7.12 (1H, NH), 5.48 (1H, H$_4$), 4.01 (2H, m), 3.80 (1H, H$_3$), 3.66 (1H, t, H$_{17}$), from 2.40 to 0.70 (m), 1.48 (s, t-Bu), 0.99 (3H, s, H$_{19}$), 0.76 (3H, s, H$_{18}$). $^{13}$C NMR (CDCl$_3$): δ 170.8, 168.6, 151.6, 117.5, 82.2, 81.6, 72.8, 67.6, 53.8, 50.5, 42.9, 41.3, 37.6, 36.6, 35.8, 32.3, 32.2, 32.0, 30.3, 28.0, 24.3, 23.3, 21.0, 18.1, 11.1.

7.2 Preparation of the Testosterone Derivative of Formula (Ibα)

440 mg (0.95 mmol) of the product synthesized (VIα, m=n=1) is dissolved in 30 ml of methanol and a transparent solution is formed. 3 ml of sodium hydroxide solution (NaOH, 1.0 N) is added at room temperature. Stirring is maintained for 4 hours. There is no longer presence of the starting product (VIα) in TLC (eluent: chloroform/methanol, 4/1, v/v). The reaction mixture is neutralized with hydrochloric acid (HCl, 1.0 N) at pH=6 and evaporated at 25° C. under reduced pressure. The residue is purified with a silica gel chromatography column (eluent: chloroform/methanol, 2.5/1, v/v). 380 mg (yield=98.6%) of the product (Iα) is obtained.

$^1$H NMR (CD$_3$OD): δ 7.88 (1H, t, $^2$J=3.13 Hz, NH), 5.50 (1H, d, $^2$J=4.06 Hz, H$_4$), 4.00 (2H, d, $^2$J=3.13 Hz), 3.90 (2H, s), 3.80 (1H, t, H$_3$), 3.56 (1H, t, H$_{17}$), from 2.40 to 0.70 (m), 1.02 (3H, s, H$_{19}$), 0.76 (3H, s, H$_{18}$). $^{13}$C NMR (CD$^3$OD): δ 174.2, 173.5, 152.5, 119.0, 82.4, 74.0, 68.3, 55.4, 52.0, 44.0, 42.5, 38.7, 37.9, 37.2, 33.7, 33.4, 33.2, 30.6, 25.3, 24.3, 22.2, 18.6, 11.6. IR (cm$^{-1}$): 3369, 2921, 2847, 1715, 1624, 1538, 1436, 1422, 1233, 1078. MS (LC-MS): 404.4 (M-H)$^-$, 809.9 (2M-H)$^-$.

Example 8

Preparation of a Testosterone Derivative of the Invention of Formula (Iα)

compound of formula (Iα) in which m=n=1 and Y=

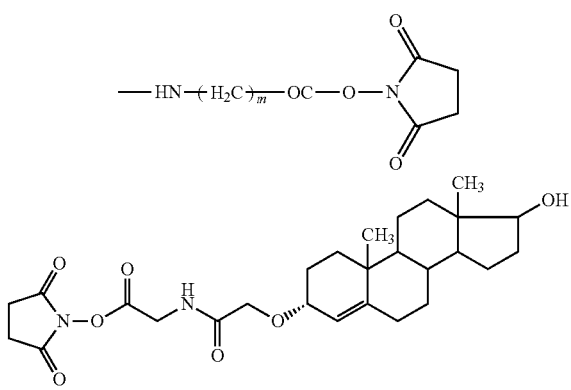

The procedure described in example 7 was repeated, then continuing as follows.

The product of formula (Ibα) prepared in example 7 (120 mg, 0.295 mmol) is dissolved in 10 ml of anhydrous 1,2-dimethoxyethane (DME) in a flask equipped with magnetic stirring. 35.1 mg (0.295 mmol) of N-hydroxysuccinimide (HOSu) is added and a transparent solution is formed. 61.7 mg (0.295 mmol) of 1,3-dicyclohexylcarbodiimide (DCC) is added. The mixture is stirred at room temperature for 4 hours 30 min. The reaction mixture is filtered and the filtrate is evaporated without heating using a rotary evaporator. The residue obtained is washed with 6.0 ml of anhydrous dichloromethane, and then dried under vacuum. 90.4 mg (yield=61.0%, purity 85% in HPLC) of the product (Ia) is obtained. The product is stored at −20° C. under nitrogen.

$^1$H NMR (CDCl$_3$): δ 7.17 (1H, NH), 5.42 (1H, H$_4$), 4.45 (2H, d), 4.03 (2H, s), 3.76 (1H, H$_3$), 3.62 (1H, t, H$_{\alpha}$), 2.84 (4H, s), from 2.30 to 0.80 (m), 1.05 (3H, s, H$_{19}$), 0.75 (3H, s, H$_{18}$). $^{13}$C NMR (CDCl$_3$): δ 171.2, 168.7, 165.7, 152.0, 117.4, 81.9, 73.1, 67.5, 53.9, 50.6, 43.0, 38.3, 37.7, 36.6, 35.8, 32.4, 32.3, 32.1, 30.5, 25.6, 24.3, 23.4, 21.1, 18.2, 11.1.

Example 9

Preparation of a Conjugate 1 of the Invention 17β-Hydroxy-3β-Carboxymethoxyandrost-4-ene/Alkaline Phosphatase 0.3 ml of a solution of recombinant alkaline phosphatase (ALP) at 20 mg/ml (Roche, Ref. 03-535-452) is dialyzed in Spectra/Por® tubing (cutoff threshold 6000-8000 Da, Spectrum Laboratories, USA) against 300 ml of borate buffer 50 mM pH 7.6, with magnetic stirring, overnight at 2-8° C. At the end of dialysis, the concentration of the protein is determined by reading the optical density at 280 nm and this concentration is adjusted to 8 mg/ml.

The ester 17-β-hydroxy-3-β-carboxymethoxyandrost-4-ene-N-hydroxysuccinimide (or NHS) obtained in example 2 is taken up in dimethylformamide (DMF) at a concentration of 1 mg/ml.

For coupling of type (1-3) (1 mole of alkaline phosphatase-3 moles of testosterone derivative), 312.5 μl of the solution of ALP is mixed with 30 μl of the solution of ester 17-β-hydroxy-3-β-carboxymethoxyandrost-4-ene-NHS. For coupling of type (1-5), 312.5 pd of the solution of ALP is mixed with 50 μl of the solution of ester. The mixtures are incubated for 1 h on a water bath at 30° C., with gentle magnetic stirring.

Next, the reaction is blocked by adding 1 mM lysine diluted in water. The amount of lysine added is equimolar with the amount of ester used for coupling. Therefore 68 μl of the solution of lysine is added for the coupling of type (1-3) and 112 μl for the coupling of type (1-5). The mixtures are incubated for 20 min on a wheel, at 18/25° C.

After stopping the reaction, the conjugates are dialyzed in Spectra/Por® tubing (cutoff threshold about 7000 Da) for 1 h at 18/25° C. against 250 ml of Tris buffer 50 mM pH 7.4, NaCl 9 g/l, MgCl$_2$ 5 mM, ZnCl$_2$ 0.1 mM, azide 0.9 g/l, with magnetic stirring. After 1 h, the tubings are transferred to new baths, always containing 250 ml of the same buffer. Dialysis is continued overnight at 2/8° C., with magnetic stirring.

At the end of dialysis, the volume of the conjugates is made up to 1 ml with dialysis buffer. The conjugates are then purified by hydrophobic-interaction chromatography using a RESOURCE Phenyl column (Cat No. 17-1186-01, GE Healthcare Lifesciences) installed in an ÄKTA chromatography chain. The pump flow rate is set at 0.5 ml/min. The buffer TA is Tris 50 mM pH 7.4, NaCl 9 g/l, MgCl$_2$ 5 mM, ZnCl$_2$ 0.1 mM, azide 0.9 g/l, (NH$_4$)$_2$SO$_4$ 0.8M. The buffer TB is Tris 50 mM pH 7.4, NaCl 9 g/l, MgCl$_2$ 5 mM, ZnCl$_2$ 0.1 mM, azide 0.9 g/l, this is the dialysis buffer.

The RESOURCE Phenyl column is equilibrated in buffer TA. The conjugate to be purified is mixed volume for volume (475 μl conjugate and 475 μl buffer) with the buffer Tris 50 mM pH 7.4, NaCl 9 g/l, MgCl$_2$ 5 mM, ZnCl$_2$ 0.1 mM, azide 0.9 g/l, (NH$_4$)$_2$SO$_4$ 1.6 M. This step gives the conjugate in buffer TA. Injection of the conjugate is followed by washing of 30 ml in buffer TA. Then a gradient from 0 to 100% of TB is applied for 30 ml, then washing in buffer TB for 10 ml and washing in water for 10 ml. The progress of chromatography is monitored by measuring the optical density at 280 nm. The fractions starting from 42 ml of elution and up to 51 ml (i.e. 10 ml in total) are recovered, combined and then concentrated by diafiltration using an Amicon cell (Amicon stirred cells, Millipore), an Amicon PM membrane with a cutoff threshold of 10 000 Da and the buffer TB. During this step, the volume of the solution of conjugate is reduced to about 1 ml. The conjugates are stored at 2/8° C. until they are used in an immunoassay.

Example 10

Determination of Testosterone Using Conjugate 1 of the Invention 17-β-Hydroxy-3-β-Carboxymethoxyandrost-4-Ene/Alkaline Phosphatase and Comparison with Assays Using a Conjugate of the Prior Art The VIDAS® kit (bioMérieux) for testosterone assay (Cat. No 30418) was used as the reference immunoassay, it is a commercial kit with a CE mark. This assay is described in the instructions in the box ref. 09345 F-fr-2010/08 and it is carried out using the VIDAS® automatic immuno analyzer.

The disposable cone serves both as solid phase for the reaction and as pipetting system. The cartridge is made up of 10 wells covered with sealed and labeled aluminum foil. The first well comprises a precut part to facilitate introduction of the sample. The last well is an optical cuvette in which the fluorescence of the substrate is measured. The various reagents required for the analysis are contained in the intermediate wells.

The cone contained in the VIDAS® kit for testosterone assay (bioMerieux Cat. No 30418) has been sensitized with a sheep anti-rabbit IgG polyclonal antibody, and then with a rabbit anti-testosterone polyclonal antibody. The surface is passivated and it is ready to use.

The sample to be assayed is put in the first well of the cartridge. Then all the steps of the assay reaction are performed automatically by the VIDAS® analyzer. The sample to be assayed is mixed with the conjugate, which is a testosterone derivative labeled with alkaline phosphatase, but in which position 3 is not modified as in the present invention. This conjugate will be called "VIDAS® Conjugate" or Conjugate of the prior art.

Competition then takes place between the testosterone present in the sample and the testosterone derivative of the conjugate for the sites of the anti-testosterone antibody fixed on the cone. The washing steps are carried out with the buffer Tris-NaCl (0.05 mol/l) pH 7.4 or with diethanolamine (1.1 mol/l) pH 9.8 and make it possible to remove the compounds that are not fixed. During the final development step, the substrate 4-methylombelliferyl phosphate is aspirated and then introduced into the cone; the enzyme of the conjugate catalyzes the reaction of hydrolysis of this substrate in 4-methylombelliferone, and the fluorescence emitted from the latter is measured at 450 nm. The value of the fluorescence signal is inversely proportional to the concentration of the testosterone present in the sample. This concentration is calculated relative to a calibration curve.

+18/25° C., washing is carried out with saline solution. Then the solution of anti-testosterone antibodies containing a saturating agent of the protein or peptide type is added (concentration of the antibody: 0.01-0.2 µg/ml). Sensitization/passivation is continued at +18/25° C. overnight. Then the cones are emptied and dried.

The cones sensitized with the antibody Ab1 are tested with the VIDAS® conjugate, diluted to 1/2.5 for the tests with the monoclonal antibody. The cones sensitized with the antibodies Ab2 and Ab3 are tested with conjugate 1 of the invention prepared in example 9. This last-mentioned conjugate is used at a concentration of 3 ng/ml for the tests with the cones sensitized with the antibody Ab2 and 2.5 ng/ml for the cones sensitized with the antibody Ab3.

The conversion to dose is performed based on a standard 10-point range manufactured by supplementing woman's serum with testosterone in ethanolic solution. The nominal concentrations of each of the points are: 0.001 ng/ml-0.03 ng/ml-0.18 ng/ml-0.41 ng/ml-0.76 ng/ml-1.29 ng/ml-1.91 ng/ml-3.82 ng/ml-7.48 ng/ml-11.55 ng/ml.

The sample volume taken for each assay is 200 µl.

The standard range was measured with each assay format. Table 1 below summarizes the results obtained as RFV signal (relative fluorescence value) and B/B0% ratio, for the dilutions of the standard range. The ratio B/B0 is the signal obtained for the range point tested divided by the signal obtained for the range point 0.001 ng/ml of testosterone, multiplied by 100.

TABLE 1

| [c] Testosterone (ng/ml) | REF = VIDAS ® kit | | Ab1 + VIDAS ® Conjugate | | Ab2 + Conjugate 1 of the invention | | Ab3 + Conjugate 1 of the invention | |
|---|---|---|---|---|---|---|---|---|
| | Signal (RFV) | B/B0% | Signal (RFV) | B/B0% | Signal (RFV) | B/B0% | Signal (RFV) | B/B0% |
| 0.001 | 4202 | 100 | 4799 | 100 | 4077 | 100 | 3209 | 100 |
| 0.03 | 3630 | 86 | 4412 | 92 | 3490 | 86 | 2492 | 78 |
| 0.18 | 3056 | 73 | 3537 | 74 | 2935 | 72 | 1700 | 53 |
| 0.41 | 2645 | 63 | 3093 | 64 | 2527 | 62 | 1403 | 44 |
| 0.76 | 2440 | 58 | 3320 | 69 | 2238 | 55 | 1286 | 40 |
| 1.29 | 2057 | 49 | 2940 | 61 | 1880 | 46 | 960 | 30 |
| 1.91 | 1939 | 46 | 2836 | 59 | 1729 | 42 | 990 | 31 |
| 3.82 | 1493 | 36 | 2391 | 50 | 1264 | 31 | 644 | 20 |
| 7.48 | 1183 | 28 | 2163 | 45 | 905 | 22 | 380 | 12 |
| 11.55 | 880 | 21 | 1849 | 39 | 632 | 16 | 205 | 6 |

For the other assays, we used the reagents of the VIDAS® testosterone kit (Cat. No 30418) and the assay protocol given in the instructions with the kit, with the following modifications:

Cones were sensitized with other anti-testosterone antibodies: 2 mouse monoclonal immunoglobulins G (IgG), the clones 19E10H6 and 15H9H10 (bioMerieux), which will be called Ab1 and Ab2 respectively, and 1 sheep monoclonal IgG, the clone testo3.6A3 (Bioventix), which will be called Ab3. As in the cone of the format of the reference assay, the anti-testosterone antibodies were captured by anti-species polyclonal antibodies adsorbed on the cone beforehand. It is a sheep anti-mouse IgG polyclonal antibody for Ab1 and Ab2, and a donkey anti-sheep IgG polyclonal antibody for Ab3. The anti-species antibodies are diluted to a concentration between 1 and 12 µg/ml in the sensitizing solution. After incubation for 6 h at The B/B0% ratio values are shown in FIG. 1 in a graph that gives these values as a function of the logarithm of the concentration of the points of the standard range for each format, namely two formats using a conjugate of the prior art ((i) REF which is the reference assay of the prior art which corresponds to the VIDAS® commercial kit for testosterone assay (bioMerieux, Cat. No 30418), and (ii) Ab1+VIDAS® Conjugate), and two formats using a conjugate 1 of the invention (Ab2+Conjugate 1 of the invention, and Ab3+Conjugate 1 of the invention).

The graph in FIG. 1 shows that the two assay formats that are the most sensitive are those using the conjugate of the invention. In fact, the most sensitive assay format is the format combining the antibody Ab3 and Conjugate 1 of the invention. A 50% decrease in the signal is observed starting from about 0.2 ng/ml of testosterone. For the format combining the antibody Ab2 and Conjugate 1 of the invention, as well as the reference assay on VIDAS®, about 1 ng/ml of testosterone is required to reach a B/B0 ratio of 50%. The format Ab2+Conjugate 1 of the invention is slightly more sensitive than the reference format. Finally, with the format Ab1+VIDAS® Conjugate, 3.82 ng/ml of testosterone is required to reach 50%. It is the least sensitive format.

Secondly, to confirm that the format Ab2+Conjugate 1 of the invention is far more sensitive than the reference format REF, VIDAS® Testosterone kit, for which the measurement range recommended in the instructions extends from 0.1 to 13 ng/ml, these two formats were compared against serum samples obtained from the Etablissements Français du Sang (the French National Blood Service). These were 4 samples collected from women (codes with F), for whom the serum testosterone level is below 1 ng/ml, and 2 samples collected from men (codes with M). The results are presented in Table 2. The theoretical concentration was determined by a third-party laboratory, by a technique that gives accurate measurement of concentrations below 1 ng/ml such as ID/GC-MS mass spectrometry. The ratio [c] measured/[c] theoretical×100 presented in Table 2 for each assay provides an assessment of the accuracy of each assay, [c] signifying concentration. The closer this ratio is to 100%, the more accurate the assay.

TABLE 2

| Sample code | [c] theoretical | REF = VIDAS ® Kit | | Ab2 + Conjugate 1 of the invention | |
|---|---|---|---|---|---|
| | | [c] measured | [c] me/ [c] th ×100 | [c] measured | [c] me/ [c] th ×100 |
| F37 | 0.11 | 0.25 | 223 | 0.13 | 118 |
| F38 | <0.025 | 0.09 | 340 | 0.03 | 100 |
| F45 | 0.07 | 0.20 | 279 | 0.07 | 100 |
| F46 | 0.21 | 0.41 | 193 | 0.30 | 140 |
| M29 | 2.38 | 3.20 | 134 | 2.97 | 125 |
| M34 | 3.94 | 3.35 | 85 | 4.05 | 103 |

The results in Table 2 show that the format using a conjugate of the invention is more accurate than the reference assay on VIDAS®, especially for assay of the low levels of serum testosterone found in women.

Example 11

Preparation of Conjugate 2 of the Invention 17-β-Hydroxy-3-β-Carboxymethoxyandrost-4-ene/Biotin The molecule will be abbreviated here to testosterone-3β-EMC-DAP-biotin, DAP being diaminopropyl, and has the following formula.

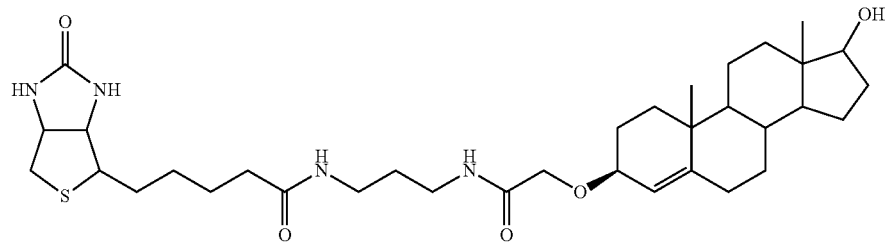 [SMILES: CC12CC[C@H](OCC(=O)NCCCNC(=O)CCCCC3SCC4NC(=O)NC43)C=C1CCC1C2CCC2(C)C(O)CCC12]

In a 50-ml flask equipped with magnetic stirring, 100 nag (0.287 mmol) of 17-β-hydroxy-3β-carboxymethoxyandrost-4-ene acid obtained in example 1 is dissolved in 7 ml of dimethoxyethane (DME) anhydride. 50 mg of N-hydroxysuccinimide (NHS) is added and stirring is maintained at room temperature for 3 min. 69 mg (0.334 mmol) of N,N'-dicyclohexylcarbodiimide (DCC) is added and a transparent solution is obtained. The reaction mixture is stirred at room temperature overnight.

The reaction mixture is filtered and the filtrate thus obtained is used directly. 100 mg (0.241 mmol) of N-(+)-biotinyl-3-aminopropylammonium trifluoroacetate (biotin-NH-DAP, TFA salt, Sigma-Aldrich Cat. No. 71776) is mixed with 1.5 ml of 1N NaHCO$_3$ solution and then added to the filtrate. Stirring is maintained at room temperature for 14 h.

The reaction mixture is dried at room temperature under reduced pressure. The residue obtained is purified by chromatography on silica gel 60 (0.040-0.063 mm, Merck Cat. No. 109385) with the eluent: dichloromethane/methanol, 8/1, v/v to start and dichloromethane methanol, 5/1, v/v to finish the purification. 125 mg of product is obtained, which corresponds to a yield of 82%. Testosterone-3β-EMC-DAP-biotin is a white powder.

The product is analyzed by high-performance liquid chromatography (HPLC). The column used is a Thermokromasil C18, 150×4.6 mm and the eluent is a mixture of acetonitrile, water (0.1% trifluoroacetic acid) in a gradient. The chromatography is monitored by measuring the absorbance at 214 nm. The product purity determined in this way is 90.1%.

Example 12

Determination of Testosterone Using Conjugate 2 of the Invention Testosterone-3β-EMC-DAP/Biotin 100 μl/well of the mouse anti-goat Fe IgG monoclonal antibody (clone 9A4A5, bioMerieux) diluted to 10 μg/ml in PBS buffer 1× is distributed in a 96-well microplate (Nunc Maxisorp F96). The microplate is incubated overnight at room temperature in order to obtain adsorption of the antibody. The microplate is emptied, and then 300 μl/well of passivating buffer (buffer Tris 0.2 M pH 6.2) containing a saturating agent of the protein or peptide type, and the sheep anti-testosterone monoclonal antibody clone 3.6A3 (Ab3-bioVentix) diluted to 0.2 μg/ml are added. The microplate is incubated for 1 h at 37° C. Three washings are carried out with TBS (Tris buffered saline)-Tween®-20 0.05%. The range points used in example 10 are diluted to 1/2 in Tris buffer; 100 μl of these dilutions are distributed in the wells of the plate. After incubation for 1 h at 37° C., the wells are emptied and 0.2 ng/well of Conjugate 2 of the invention testosterone-3β-EMC-DAP-biotin in Tris buffer is added. The reaction with the conjugate is carried out for 15 minutes at 37° C., and is followed by 3 washings. 100 μl/well of streptavidin-peroxidase solution (Jackson Immunoresearch Cat. No. 016-30-084) diluted to 1/20 000 in TBS-Tween®-20 0.05%, BSA 2% is added and the microplate is incubated for 30 min at 37° C. After 3 washings, 100 µl/well of the 1-step Ultra TMB substrate (Thermo Scientific, Cat. No. 34028) is added and the microplate is incubated for 5 min at room temperature, away from the light. The reaction is then stopped by adding 100 µl of 2M sulfuric acid. The optical density (OD) at 450 nm and at 630 nm is measured in a microplate reader. For each well, the optical density at 630 nm is subtracted from the optical density at 450 nm. The results obtained on applying this protocol are presented in Table 3.

TABLE 3

| [c] Testosterone (ng/ml) | OD$_{450}$-OD$_{630}$ | B/B0% |
| --- | --- | --- |
| 0.001 | 2.52 | 100 |
| 0.03 | 2.10 | 83 |
| 0.18 | 1.88 | 74 |
| 0.41 | 1.61 | 64 |
| 0.76 | 1.36 | 54 |
| 1.29 | 1.00 | 40 |
| 3.82 | 0.42 | 17 |
| 11.55 | 0.17 | 7 |

The values of the B/B0% ratio from Table 3 are shown in FIG. 2 as a graph that gives these values as a function of the logarithm of the concentration of the points of the standard range. FIG. 2 gives the values obtained in example 10 for the format using Ab2+Conjugate 1 of the invention.

This graph shows that the character of the testosterone assay range obtained with the antibody Ab3+Conjugate 2 of the invention testosterone-3β-EMC-DAP-biotin on the microplate is comparable to that obtained with the format Ab2+Conjugate 1 of the invention on VIDAS® in example 10. This microplate assay with a conjugate of the invention is therefore more sensitive than the VIDAS® assays using the VIDAS® Conjugate.

BIBLIOGRAPHIC REFERENCES

Cekan, S. Z., 1979, J. Steroid Biochem., II: 1629.
Cook B and Bestall G. H., 1987, Steroid hormones a practical approach, Ed Green B. and Leake R. E., Chapter 1.
Demers L. M., 2010, Maturitas, 67: 39-45.
Fiet J et al., 2004, Steroids, 69(7): 461-471.
Litwack G., 1992, Biochemistry of Hormones II: Steroid hormones. In DEVLIN T. M., Textbook of Chemistry with clinical correlations, 3rd Edition, Wiley J. and Sons, 901-925.
Moneti G; et al., 1987, J. Steroid Biochem., 27(1-3): 53.
Rassasie, M. J., et al., 1992, Steroids, 57: 112.
Rosner W. et al., 2007, JCEM, 92(2): 405-413.
Owen, W. E., et al., 2010, Clinica Chimica Acta, 411: 1073.
Stabler T. V., et al., 1991, Clin. Chem., 37(11): 1987.
Thienpont, L. M., et al., 2008, Clin. Chem., 54(8):1290.
Uesehiba, H. et al., 1991, Clin. Chem., 37(8): 1329.
Vingler P., et al., 1991, J. of Chromatography, 571: 73.
Wong, S. S., 1991, Reactive groups of proteins and their modifying agents. In Chemistry of protein conjugation and cross-linking, CRC Press Inc, p 33-39.
Wudy, S. A., et al., 1992, Steroids, 57: 319.

The invention claimed is:

1. A testosterone derivative of formula (I):

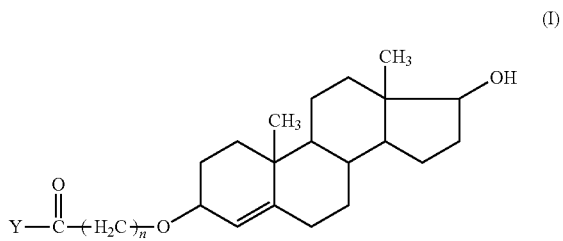

wherein:

n is an integer in a range of from 1 to 10; and

Y is selected from the group consisting of —OH, —NH—(CH$_2$)$_m$—COOH, —N$_3$,

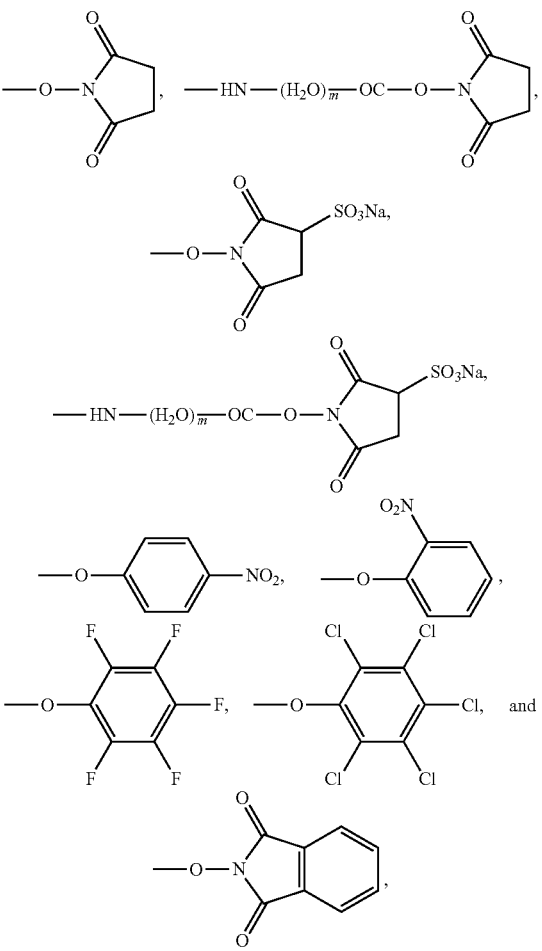

where m is an integer in a range of from 1 to 10.

2. The testosterone derivative as claimed in claim 1, wherein n is in a range of from 1 to 5.

3. The testosterone derivative as claimed in claim 1, wherein Y is selected from the group consisting of:

—OH,

—NH—(CH$_2$)$_m$—COOH, and

―HN―(H₂C)ₘ―OC―O―N(succinimide) , where m is in a range of 1 to 10.

4. The testosterone derivative as claimed in claim 1, in a form of a derivative at the carbon in position 3.

5. The testosterone derivative as claimed in claim 1, in a form of an α derivative at the carbon in position 3.

6. A conjugate comprising the testosterone derivative as claimed in claim 1 and a marker, wherein the marker is conjugated through Y of the testosterone derivative of formula (I).

7. A method for determining a concentration of testosterone in a biological sample, the method comprising:

bringing into contact, within the sample:
 an anti-testosterone antibody or fragment thereof; and
 a compound selected from the group consisting of the testosterone derivative as claimed in claim 1 and a conjugate comprising the testosterone derivative and a marker; one of the anti-testosterone antibody or fragment thereof and the compound being adapted to emit a signal; and measuring an intensity of the signal.

8. A method for determining a concentration of testosterone by competitive immunoassay in a biological sample, comprising:

a) bringing into contact, within said sample:
 (i) an anti-testosterone antibody or fragment thereof; and
 (ii) a compound selected from the group consisting of the testosterone derivative as claimed in claim 1 and a conjugate comprising the testosterone and a marker, one of the anti-testosterone antibody or fragment thereof (i) and the compound (ii) being adapted to emit a signal, b) optionally waiting a sufficient time to allow a competition reaction, and c) measuring an intensity of the signal and determining the concentration of testosterone by comparing the measured intensity of the signal with a calibration curve establishing a relationship between the measured intensity of the signal and the testosterone concentration.

9. The method as claimed in claim 8, wherein the compound (ii) is the conjugate.

10. A diagnostic kit for implementing the method as claimed in claim 8, comprising the testosterone derivative or the conjugate.

11. A method for preparing the testosterone derivative of formula (I) as claimed in claim 1, comprising preparing a compound of formula (Ia):

(Ia)

where n is an integer in a range of from 1 to 10.

12. A method for preparing a testosterone derivative, in a form of a β isomer in position 3, of formula (Iaβ):

(Iaβ)

where n is an integer in a range of from 1 to 10, the method comprising:

reacting testosterone with acetic anhydride to protect the OH function of position 17, and then reacting with a reducing agent, in the presence of a solvent, to reduce the carbonyl in position 3 and obtain a compound of formula (IIβ):

(IIβ)

where Ac represents —CO—CH₃, and reacting the compound of formula (IIβ) with a compound of formula (III): $N_2CH-(CH_2)_{n-1}-COOC_2H_5$, and then reacting with a base, in the presence of a solvent, to obtain the testosterone derivative of formula (Iaβ).

13. A method for preparing a testosterone derivative, in a form of a β isomer in position 3, of formula (Ibβ):

(Ibβ)

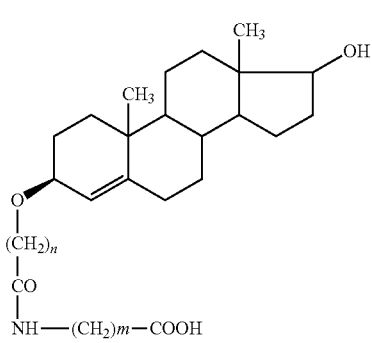

where:
n is an integer is a range of from 1 to 10, and
m is an integer in a range of 1 to 10,
the method comprising:
reacting testosterone with acetic anhydride to protect the OH function of position 17, and then reacting with a reducing agent, in the presence of a solvent, to reduce the carbonyl in position 3 and obtain a compound of formula (IIβ):

(IIβ)

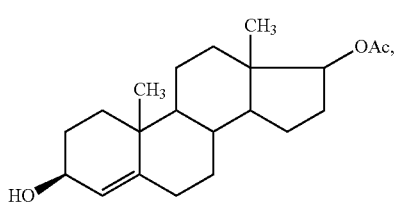

where Ac represents —CO—CH$_3$,
reacting the compound of formula (IIβ) with a compound of formula (III): N$_2$CH—(CH$_2$)$_{n-1}$—COOC$_2$H$_5$, and then reacting with a base, in the presence of a solvent, to obtain a compound of formula (Iaβ):

(Iaβ)

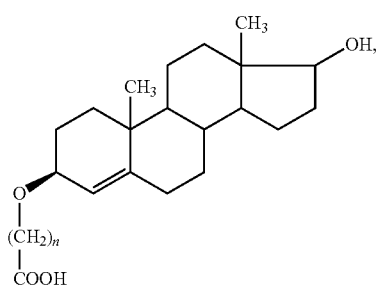

reacting the compound of formula (Iaβ) with N-hydroxy-succinimide, in the presence of a carbodiimide derivative, to produce a compound of formula (IVβ):

(IVβ)

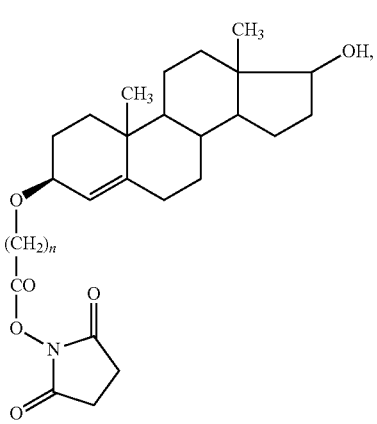

reacting the compound of formula (IVβ) with a compound of formula (V): H$_2$N—(CH$_2$)m-COOR$_1$, where R$_1$ is an alkyl or aryl group, to produce a compound of formula (VIβ):

(VIβ)

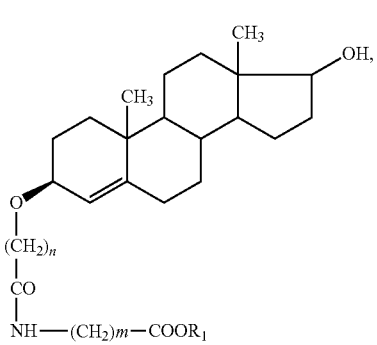

and
reacting the compound of formula (VIβ) with a base, in the presence of a solvent, to obtain the testosterone derivative of formula (Ibβ).

14. A method for preparing a testosterone derivative, in a form of a β isomer in position 3, of formula (Iβ):

(Iβ)

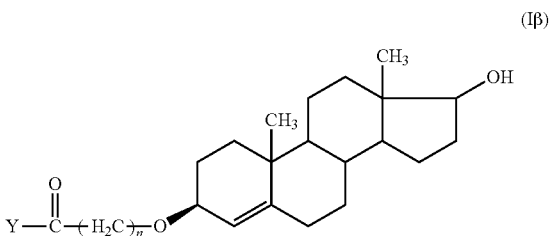

where:
n is an integer in a nine of from 1 to 10, and
Y represents a moiety selected from the group consisting of:

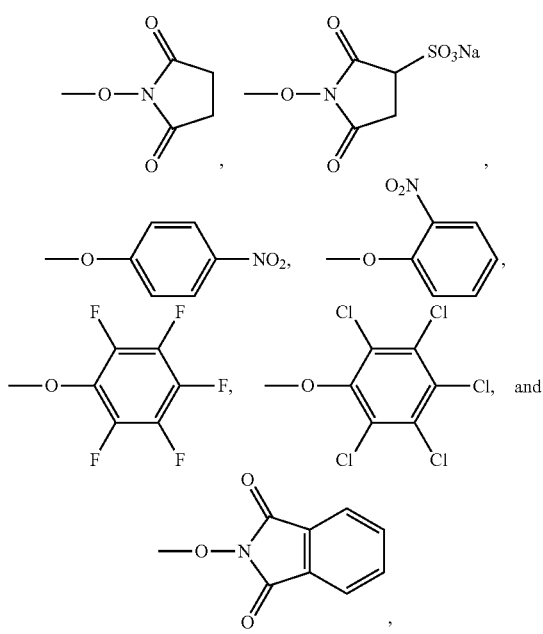

the method comprising:
reacting testosterone with acetic anhydride to protect the OH function of position 17, and then reacting with a reducing agent, in the presence of a solvent, to reduce the carbonyl in position 3 and obtain a compound of formula (IIβ):

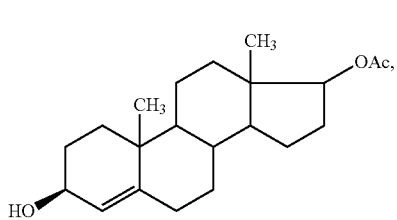

where AC represents —CO—CH$_3$,
reacting the compound of formula (IIβ) with a compound of formula (III): N$_2$CH—(CH$_2$)$_{n-1}$—COOC$_2$H$_5$, and then reacting with a base, in the presence of a solvent, to obtain a compound of formula (Iaβ):

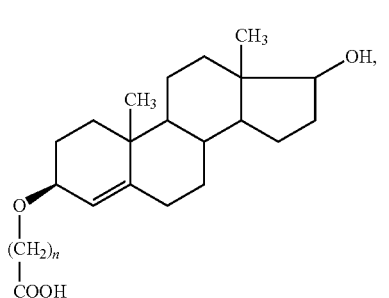

and
reacting the compound of formula (Iaβ), in the presence of a carbodiimide derivative, with a reagent to obtain the testosterone derivative of formula (Iβ), wherein the reagent is selected depending on Y from the group consisting of:

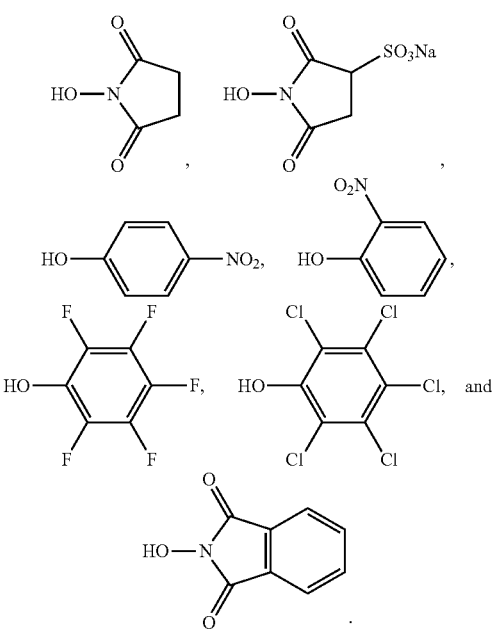

15. A method for preparing a testosterone derivative, in a form of a β isomer in position 3, of formula (Iβ):

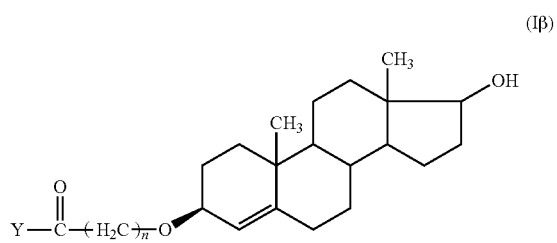

where:
n is an integer in a range of from 1 to 10; and
Y represents a moiety selected from the group consisting of:

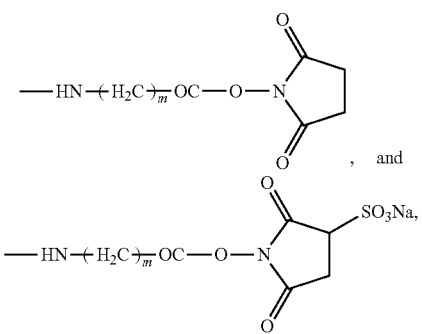

where m is an integer in a range of from 1 to 10,
the method comprising:

reacting testosterone with acetic anhydride to protect the OH function of position 17, and then reacting with a reducing agent, in the presence of a solvent, to reduce the carbonyl in position 3 and obtain a compound of formula (IIβ):

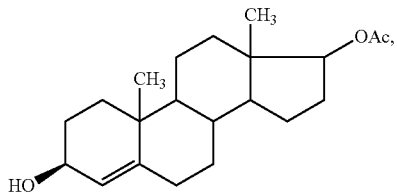
(IIβ)

where Ac represents —CO—CH$_3$, reacting the compound of formula (IIβ) with a compound of formula (III): N$_2$CH—(CH$_2$)$_{n-1}$—COOC$_2$H$_5$, and then reacting with a base, in the presence of a solvent, to obtain a compound of formula (Iaβ):

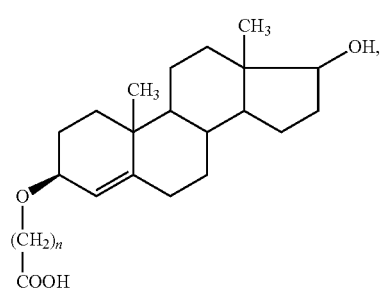
(Iaβ)

reacting the compound of formula (Iaβ) with N-hydroxy-succinimide, in the presence of a carbodiimide derivative, to produce a compound of formula (IVβ):

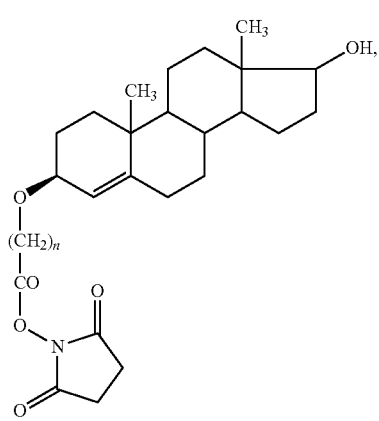
(IVβ)

reacting the compound of formula (IVβ) with a compound of formula (V): H$_2$N—(CH$_2$)m-COOR$_1$, where R$_1$ is an alkyl or aryl group, to produce a compound of formula (VIβ):

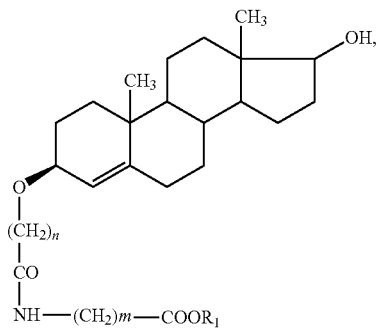
(VIβ)

reacting the compound of formula (VIβ) with a base, in the presence of a solvent, to obtain a compound of formula (Ibβ):

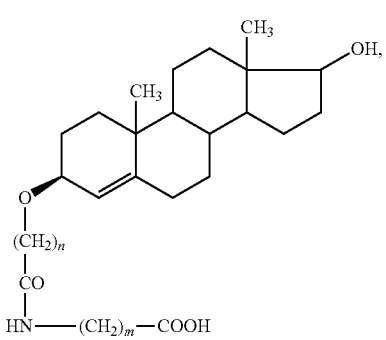
(Ibβ)

and reacting the compound of formula (Ibβ), in the presence of a carbodiimide derivative, with a reagent to obtain the testosterone derivative of formula (Iβ), wherein the reagent is selected depending on Y from the group consisting of:

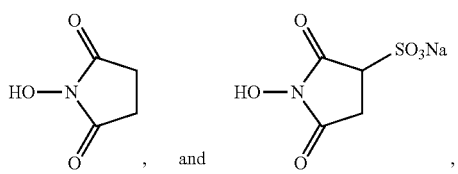
, and ,

16. A method for preparing a testosterone derivative, in a form of a β isomer in position 3, of formula (Icβ):

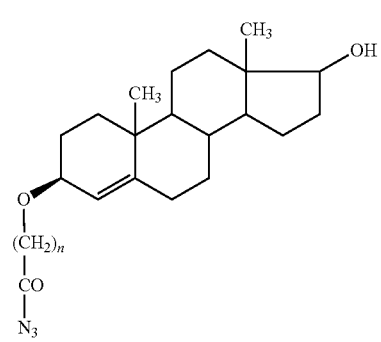
(Icβ)

where n is an integer in a range of from 1 to 10,
the method comprising:

reacting testosterone with acetic anhydride to protect the OH function of position 17, and then reacting with a reducing agent, in the presence of a solvent, to reduce the carbonyl in position 3 and obtain a compound of formula (IIβ):

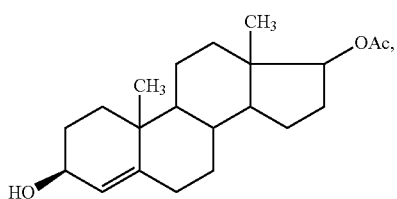

(IIβ)

where Ac represents —CO—CH$_3$, reacting the compound of formula (IIβ) with a compound of formula (III): N$_2$—CH—(CH)$_{n-1}$COOC$_2$H$_5$, and then reacting with a base, in the presence of a solvent, to obtain a compound of formula (Iaβ):

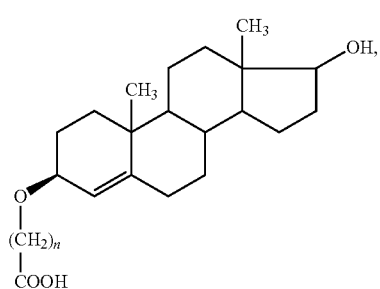

(Iaβ)

reacting the compound of formula (Iaβ), in the presence of a carbodiimide derivative, with H$_2$NNH$_2$, to obtain a compound of formula (VIIβ):

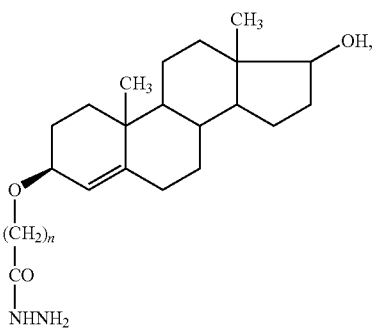

(VIIβ)

and
reacting the compound of formula (VIIβ) with HONO to obtain the testosterone derivative of formula (Icβ).

17. A method for preparing a testosterone derivative, in a form of an α isomer in position 3, of formula (Iaα):

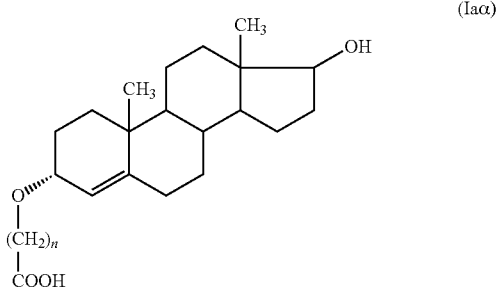

(Iaα)

where n is an integer in a range of from 1 to 10,
the method comprising:

reacting testosterone with t-butyldimethylchlorosilane to protect the OH function of position 17, and then reacting with a reducing agent, in the presence of a solvent, to reduce the carbonyl in position 3 and obtain a compound of formula (VIIIβ):

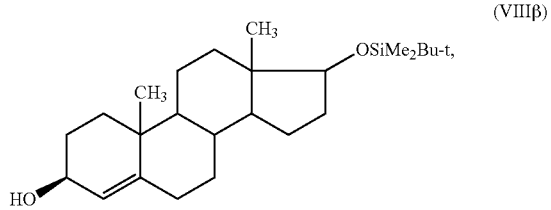

(VIIIβ)

where —SiMe$_2$Bu-t represents t-butyldimethylsilanyl, reacting the compound of formula (VIIIβ) with triphenylphosphine, benzoic acid and diethyl azodicarboxylate, and then reacting with a base, in the presence of a solvent, to transform, in position 3, the β isomer into an α isomer and obtain a compound of formula (VIIIα):

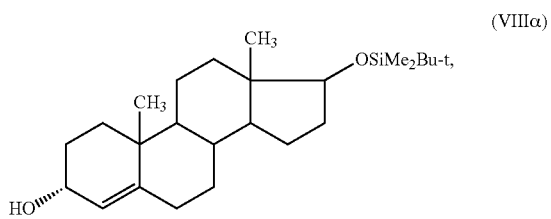

(VIIIα)

where —SiMe$_2$Bu-t represents t-butyldimethylsilanyl, and reacting the compound of formula (VIIIα) with a compound of formula (III): N$_2$CH—(CH)$_{n-1}$COOC$_2$H$_5$, and then reacting with a base, in the presence of a solvent, to obtain the testosterone derivative of formula (Iaα).

18. A method for preparing a testosterone derivative, in a form of an α isomer in position 3, of formula (Ibα):

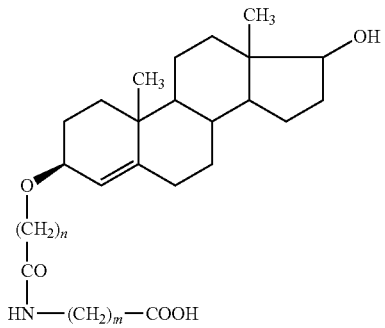

where:
n is an integer in a range of from 1 to 10, and
m is an integer in a range of from 1 to 10,
the method comprising:
reacting testosterone with t-butyldimethylchlorosilane to protect the OH function of position 17, and then reacting with a reducing agent, in the presence of a solvent, to reduce the carbonyl in position 3 and obtain a compound of formula (VIIIβ):

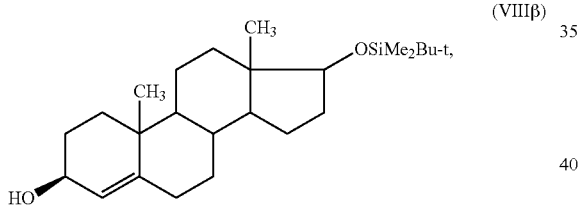

where —SiMe$_2$Bu-t represents t-butyldimethylsilanyl,
reacting the compound of formula (VIIIβ) with triphenylphosphine, benzoic acid and diethyl azodicarboxylate, and then reacting with a base, in the presence of a solvent, to transform, in position 3, the β isomer into an α isomer and obtain a compound of formula (VIIIα):

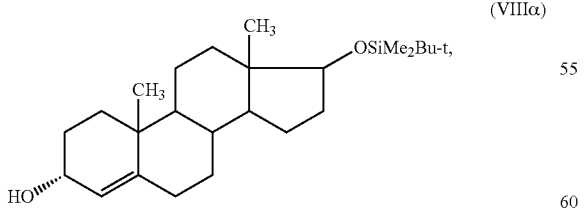

where —SiMe$_2$Bu t represents t-butyldimethylsilanyl,
reacting the compound of formula (VIIIα) with a compound of formula (III): $N_2CH—(CH_2)_{n-1}—COOC_2H_5$, and then reacting with a base, in the presence of a solvent, to obtain a compound of formula (Iaα):

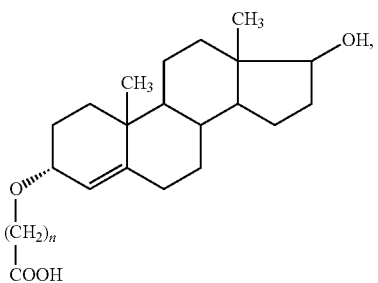

reacting the compound of formula (Iaα) with N-hydroxysuccinimide, in the presence of a carbodiimide derivative, to produce a compound of formula (IVα):

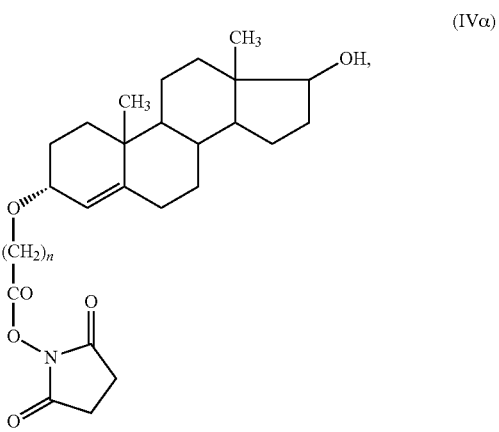

reacting the compound of formula (IVα) with a compound of formula (V): $H_2N—(CH_2)m-COOR_1$, where $R_1$ is an alkyl or aryl group, to produce a compound of formula (VIα):

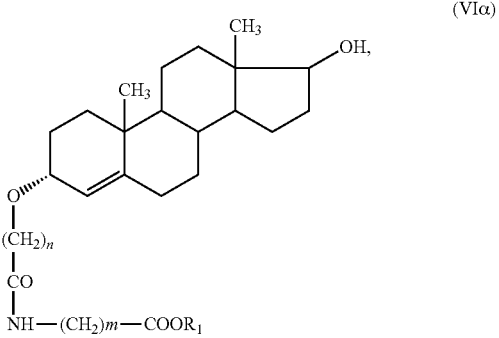

and
reacting the compound of formula (VIα) with a base, in the presence of a solvent, to obtain the testosterone derivative of formula (Ibα).

19. A method for preparing a testosterone derivative, in a form of an α isomer in position 3, of formula (Iα):

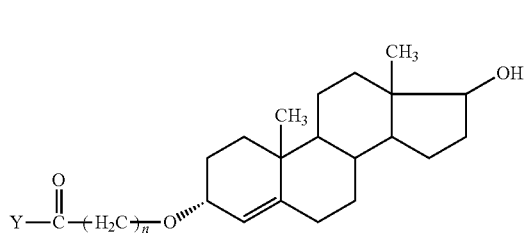

(Iα)

where:
n is an integer in a range of from 1 to 10, and
Y represents a moiety selected from the group consisting of:

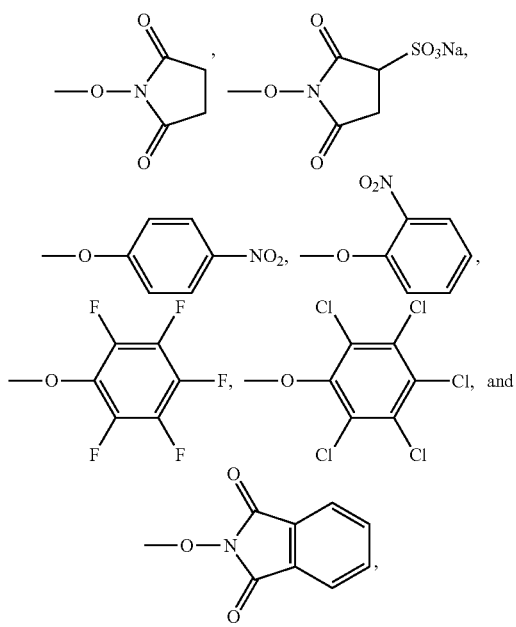

the method comprising:
reacting testosterone with t-butyldimethylchlorosilane to protect the OH function of position 17, and then reacting with a reducing agent, in the presence of a solvent, to reduce the carbonyl in position 3 and obtain a compound of formula (VIIIβ):

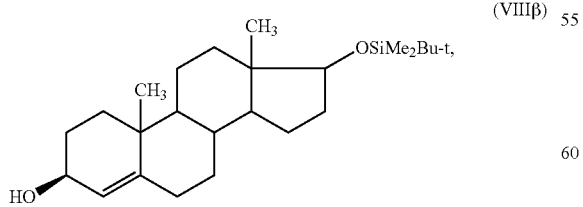

(VIIIβ)

where —SiMe$_2$Bu-t represents t-butyldimethylsilanyl,
reacting the compound of formula (VIIIβ) with triphenylphosphine, benzoic acid and diethyl azodicarboxylate, and then reacting with a base, in the presence of a solvent, to transform, in position 3, the β isomer to an α isomer and obtain a compound of formula (VIIIα):

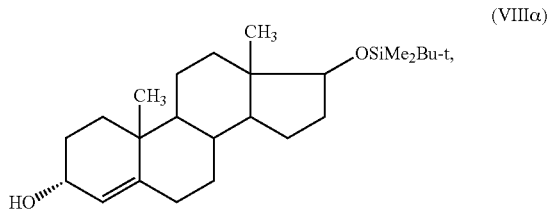

(VIIIα)

where —SiMe$_2$Bu-t represents t-butyldimethylsilanyl,
reacting the compound of formula (VIIIα) with a compound of formula (III): N$_2$CH—(CH$_2$)$_{n-1}$—COOC$_2$H$_5$, and then reacting with a base, in the presence of a solvent, to obtain a compound of formula (Iaα):

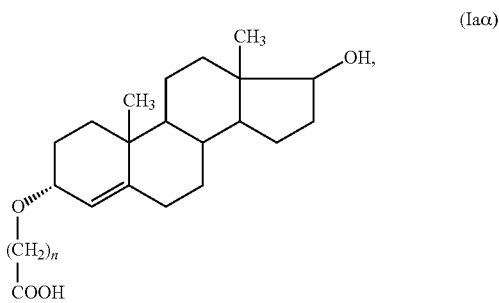

(Iaα)

reacting the compound of formula (Iaα), in the presence of a carbodiimide derivative, with a reagent to obtain the testosterone derivative of formula (Iα), wherein the reagent is selected depending on Y from the group consisting of:

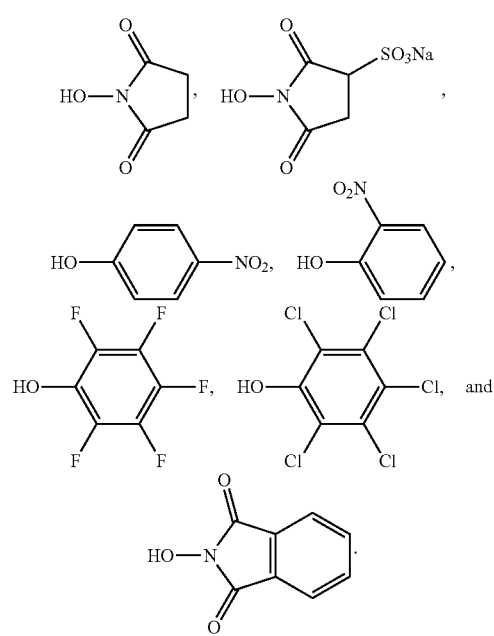

20. A method for preparing a testosterone derivative, in a form of an α isomer in position 3, of formula (Iα):

(Iα)

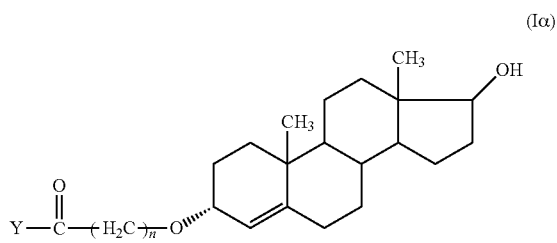

where:
n is an integer in a range of from 1 to 10, and
Y represents a moiety selected from the group consisting of:

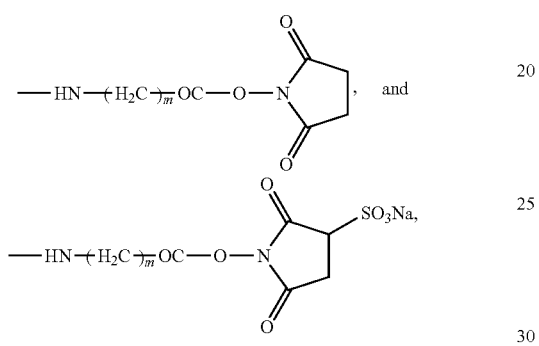

where m is an integer in range of from 1 to 10,
the method comprising:
reacting testosterone with t-butyldimethylchlorosilane to protect an OH function of position 17, and then reacting with a reducing agent, in the presence of a solvent, to reduce the carbonyl in position 3 and obtain a of formula (VIIIβ):

(VIIIβ)

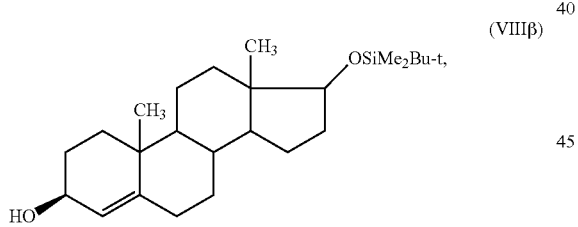

where —SiMe$_2$Bu-t represents t-butyldimethylsilanyl,
reacting the compound of formula (VIIIβ) with triphenylphosphine, benzoic acid and diethyl azodicarboxylate, and then reacting with a base, in the presence of a solvent, to transform, in position 3, the β isomer into an α isomer and obtain a compound of formula (VIIIα):

(VIIIα)

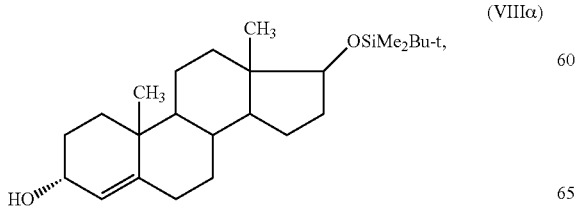

where —SiMe$_2$Bu-t t-butyldimethylsilanyl,
reacting the compound of formula (VIIIα) with a compound of formula (III): N$_2$CH—(CH$_2$)$_{n-1}$—COOC$_2$H$_5$, and then reacting with a base, in the presence of a solvent, to obtain a compound of formula (Iaα):

(Iaα)

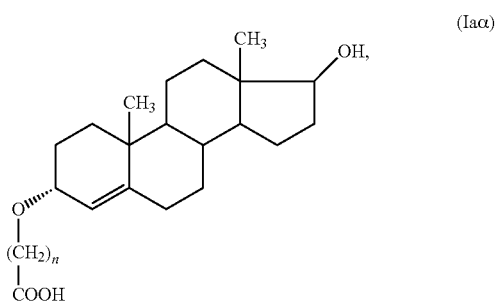

reacting the compound of formula (Iaα) with N-hydroxysuccinimide, in the presence of a carbodiimide derivative, to produce a compound of formula (IVα):

(IVα)

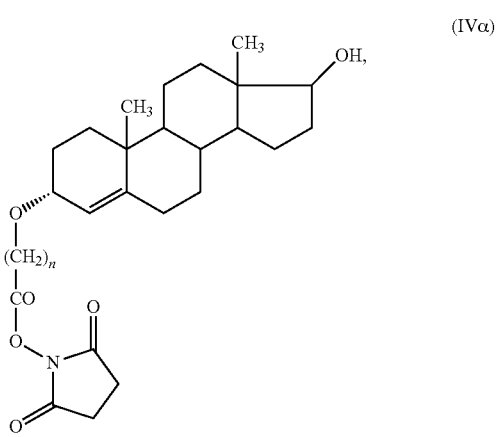

reacting the compound of formula (IVα) with a compound of formula (V): H$_2$N—(CH$_2$)m-COOR$_1$, where R$_1$ is an alkyl or aryl group, to produce a compound of formula (VIα):

(VIα)

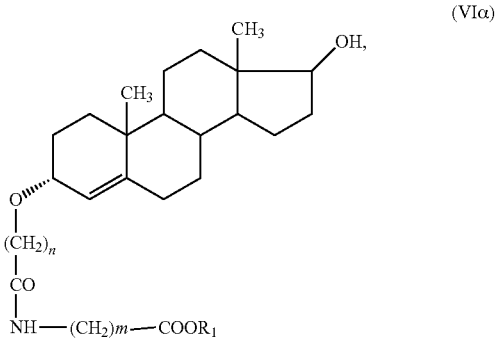

reacting the compound of formula (VIα) with a base, in the presence of a solvent, to obtain a compound of formula (Ibα):

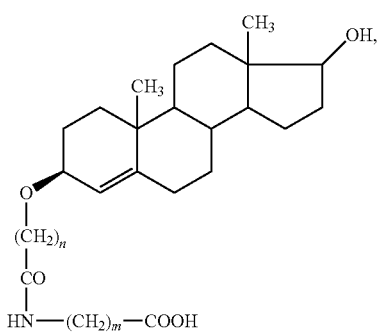

(Ibα)

and
reacting the compound of formula (Ibα), in the presence of a carbodiimide derivative, with a reagent to obtain the testosterone derivative of formula (Iα), wherein the reagent is selected depending on Y from the group consisting of:

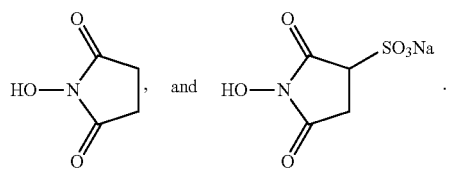

21. A method for preparing a testosterone derivative, in a form of an α isomer in position 3, of formula (Icα):

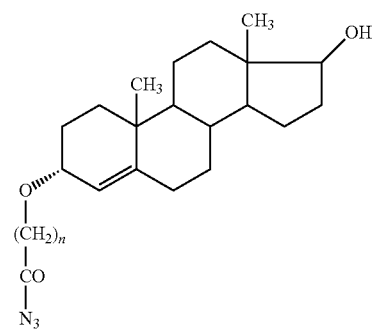

(Icα)

where n is an integer in a range of from 1 to 10,
the method comprising:
reacting testosterone with t-butyldimethylchlorosilane to protect an OH function of position 17, and then reacting with a reducing agent, in the presence of a solvent, to reduce the carbonyl in position 3 and obtain a compound of formula (VIIIβ):

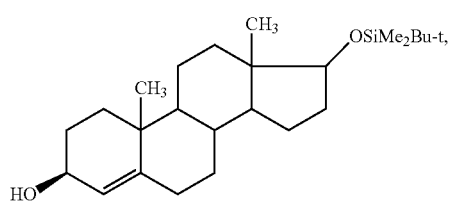

(VIIIβ)

where —SiMe$_2$Bu-t represents t-butyldimethylsilanyl,
reacting the compound of formula (VIIIβ) with triphenylphosphine, benzoic acid and diethyl azodicarboxylate, and then reacting with a base, in the presence of a solvent, to transform, in position 3, the β isomer into an α isomer and obtain a compound of formula (VIIIα):

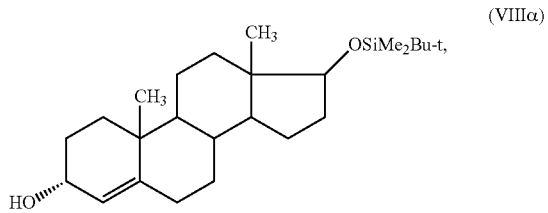

(VIIIα)

where —SiMe$_2$Bu-t represents t-butyldimethylsilanyl,
reacting the compound of formula (VIIIα) with a compound of formula (III): N$_2$CH—(CH$_2$)$_{n-1}$—COOC$_2$H$_5$, and then reacting with a base, in the presence of a solvent, to obtain a compound of formula (Iaα):

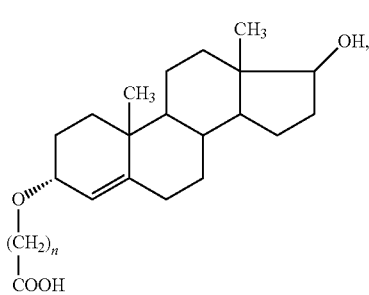

(Iaα)

reacting the compound of formula (Iaα), in the presence of a carbodiimide derivative, with H$_2$NNH$_2$, to obtain a compound of formula (VIIα):

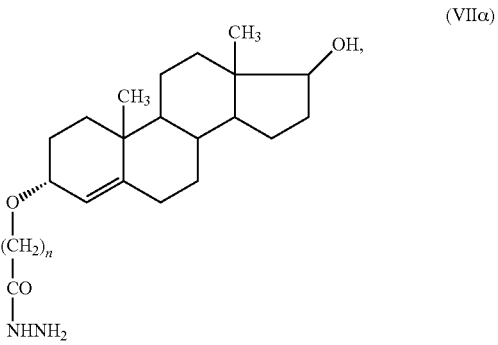

(VIIα)

and
reacting the compound of formula (VIIα) with HONO to obtain the testosterone derivative of formula (Icα).

\* \* \* \* \*